United States Patent
Gross et al.

(10) Patent No.: US 8,626,299 B2
(45) Date of Patent: Jan. 7, 2014

(54) THORACIC AORTA AND VAGUS NERVE STIMULATION

(75) Inventors: Yossi Gross, Moshav Mswazor (IL); Amir Dagan, Kibbutz Megiddo (IL); Yotam Reisner, Kiryat Tivon (IL); Offer Glasberg, Zichron Ya'akov (IL); Nitai Hanani, Haifa (IL); Gal Ariav, Givaat Ada (IL)

(73) Assignee: Enopace Biomedical Ltd. (IL)

( * ) Notice: Subject to any disclaimer, the term of this patent is extended or adjusted under 35 U.S.C. 154(b) by 65 days.

(21) Appl. No.: 12/957,799

(22) Filed: Dec. 1, 2010

(65) Prior Publication Data

US 2011/0137370 A1    Jun. 9, 2011

Related U.S. Application Data

(63) Continuation-in-part of application No. 12/792,227, filed on Jun. 2, 2010, which is a continuation-in-part of application No. PCT/IL2009/000117, filed on Jan. 29, 2009, which is a continuation-in-part of application No. 12/023,896, filed on Jan. 31, 2008, application No. 12/957,799, which is a continuation-in-part of application No. 12/851,214, filed on Aug. 5, 2010.

(60) Provisional application No. 61/183,319, filed on Jun. 2, 2009, provisional application No. 61/331,453, filed on May 5, 2010.

(51) Int. Cl.
    *A61N 1/00*    (2006.01)

(52) U.S. Cl.
    USPC .......................................................... 607/44

(58) Field of Classification Search
    USPC ............................................... 607/44, 116, 9
    See application file for complete search history.

(56) References Cited

U.S. PATENT DOCUMENTS

| 3,650,277 A | 3/1972 | Sjostrand et al. |
| 3,661,148 A | 5/1972 | Kolin |

(Continued)

FOREIGN PATENT DOCUMENTS

| EP | 0109935 A1 | 5/1984 |
| EP | 0791341 A1 | 8/1997 |

(Continued)

OTHER PUBLICATIONS

Sabba, H.N., Global Left Ventricular Remodeling with the Acorn Cardiac Support Device: Hemodynamic and Angiographic Findings in Dogs with Heart Failure, Heart Failure Reviews, 10, 109-115, 2005, 2005 Springer Science & Business Media, Inc.

(Continued)

*Primary Examiner* — Christopher D Koharski
*Assistant Examiner* — Nadia Ahmad
(74) *Attorney, Agent, or Firm* — Edwards Wildman Palmer LLP; Barry Kramer; Lisa Swiszcz

(57) ABSTRACT

Apparatus and methods are provided, including an electrode that is placed in contact with an artery of a subject. A control unit drives the electrode to perform a function with respect to the artery, the function selected from the group consisting of: driving a current into the artery, and sensing an electrical parameter of the artery. A transmitter is placed in a vein of the subject that is in a vicinity of the artery, the transmitter being wiredly connected to the control unit. The control unit is configured to drive the electrode by wirelessly transmitting a signal via the transmitter. Other embodiments are also described.

26 Claims, 16 Drawing Sheets

(56) References Cited

U.S. PATENT DOCUMENTS

| | | |
|---|---|---|
| 4,154,227 A | 5/1979 | Krause et al. |
| 4,201,219 A | 5/1980 | Bozal Gonzalez et al. |
| 4,474,630 A | 10/1984 | Planck et al. |
| 4,791,931 A | 12/1988 | Slate |
| 4,821,723 A | 4/1989 | Baker, Jr. et al. |
| 4,938,766 A | 7/1990 | Jarvik |
| 5,192,271 A | 3/1993 | Kalb et al. |
| 5,265,011 A | 11/1993 | O'Rourke |
| 5,265,601 A | 11/1993 | Mehra |
| 5,324,323 A | 6/1994 | Bui |
| 5,330,507 A | 7/1994 | Schwartz |
| 5,372,573 A | 12/1994 | Habib |
| 5,411,031 A | 5/1995 | Yomtov |
| 5,423,871 A | 6/1995 | Hoegnelid et al. |
| 5,458,626 A | 10/1995 | Krause |
| 5,487,760 A | 1/1996 | Villafana |
| 5,612,314 A | 3/1997 | Stamler et al. |
| 5,645,839 A | 7/1997 | Chobanian et al. |
| 5,649,966 A | 7/1997 | Noren et al. |
| 5,669,924 A | 9/1997 | Shaknovich |
| 5,707,400 A | 1/1998 | Terry, Jr. et al. |
| 5,762,599 A | 6/1998 | Sohn |
| 5,782,774 A | 7/1998 | Shmulewitz |
| 5,800,464 A | 9/1998 | Kieval |
| 5,800,502 A | 9/1998 | Boutos |
| 5,900,433 A | 5/1999 | Igo et al. |
| 5,902,712 A | 5/1999 | Burns et al. |
| 5,904,712 A | 5/1999 | Axelgaard |
| 5,906,641 A | 5/1999 | Thompson et al. |
| 5,913,876 A | 6/1999 | Taylor et al. |
| 5,935,077 A | 8/1999 | Ogle |
| 5,994,444 A | 11/1999 | Trescony et al. |
| 6,023,640 A | 2/2000 | Ross |
| 6,038,485 A | 3/2000 | Axelgaard |
| 6,053,873 A | 4/2000 | Govari et al. |
| 6,058,331 A | 5/2000 | King |
| 6,086,527 A | 7/2000 | Talpade |
| 6,106,477 A | 8/2000 | Miesel et al. |
| 6,120,520 A | 9/2000 | Saadat et al. |
| 6,141,587 A | 10/2000 | Mower |
| 6,200,259 B1 | 3/2001 | March |
| 6,245,103 B1 | 6/2001 | Stinson |
| 6,277,078 B1 | 8/2001 | Porat et al. |
| 6,280,377 B1 | 8/2001 | Talpade |
| 6,347,247 B1 | 2/2002 | Dev et al. |
| 6,411,845 B1 | 6/2002 | Mower |
| 6,445,953 B1 | 9/2002 | Bulkes et al. |
| 6,463,323 B1 | 10/2002 | Conrad-Vlasak et al. |
| 6,485,524 B2 | 11/2002 | Strecker |
| 6,522,926 B1 | 2/2003 | Kieval et al. |
| 6,575,994 B1 | 6/2003 | Marin et al. |
| 6,616,613 B1 | 9/2003 | Goodman |
| 6,616,624 B1 | 9/2003 | Kieval |
| 6,622,041 B2 | 9/2003 | Terry, Jr. et al. |
| 6,632,991 B2 | 10/2003 | Chen |
| 6,647,287 B1 | 11/2003 | Peel, III et al. |
| 6,721,603 B2 | 4/2004 | Zabara et al. |
| 6,810,286 B2 | 10/2004 | Donovan et al. |
| 6,824,561 B2 | 11/2004 | Soykan et al. |
| 6,845,267 B2 | 1/2005 | Harrison et al. |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst |
| 6,939,345 B2 | 9/2005 | KenKnight et al. |
| 6,947,792 B2 | 9/2005 | Ben-Haim et al. |
| 6,985,774 B2 | 1/2006 | Kieval et al. |
| 7,044,981 B2 | 5/2006 | Liu et al. |
| 7,062,318 B2 | 6/2006 | Ben-Haim et al. |
| 7,082,336 B2 | 7/2006 | Ransbury et al. |
| 7,090,648 B2 | 8/2006 | Sackner et al. |
| 7,158,832 B2 | 1/2007 | Kieval et al. |
| 7,167,751 B1 | 1/2007 | Whitehurst et al. |
| 7,206,637 B2 | 4/2007 | Salo |
| 7,225,019 B2 | 5/2007 | Jahns et al. |
| 7,229,403 B2 | 6/2007 | Schock et al. |
| 7,269,457 B2 | 9/2007 | Shafer et al. |
| 7,291,113 B2 | 11/2007 | Satoh et al. |
| 7,292,886 B1 | 11/2007 | Kroll |
| 7,299,091 B2 | 11/2007 | Barrett et al. |
| 7,389,149 B2 | 6/2008 | Rossing et al. |
| 7,395,119 B2 | 7/2008 | Hagen et al. |
| 7,452,334 B2 | 11/2008 | Gianchandani et al. |
| 7,476,200 B2 | 1/2009 | Tal |
| 7,486,991 B2 | 2/2009 | Libbus et al. |
| 7,614,998 B2 | 11/2009 | Gross et al. |
| 7,623,926 B2 | 11/2009 | Rossing et al. |
| 7,706,884 B2 | 4/2010 | Libbus |
| 7,706,886 B2 | 4/2010 | Morimoto et al. |
| 7,747,302 B2 | 6/2010 | Milledge et al. |
| 7,765,000 B2 | 7/2010 | Zhang et al. |
| 7,811,221 B2 | 10/2010 | Gross |
| 2001/0044434 A1 | 11/2001 | Lee et al. |
| 2002/0016615 A1 | 2/2002 | Dev et al. |
| 2002/0026228 A1 | 2/2002 | Schauerte |
| 2002/0032468 A1 | 3/2002 | Hill et al. |
| 2002/0077554 A1 | 6/2002 | Schwartz et al. |
| 2002/0103454 A1 | 8/2002 | Sackner et al. |
| 2002/0169413 A1 | 11/2002 | Keren et al. |
| 2003/0036773 A1 | 2/2003 | Whitehurst et al. |
| 2003/0050683 A1 | 3/2003 | Boutos |
| 2003/0060858 A1 | 3/2003 | Kieval et al. |
| 2003/0130715 A1 | 7/2003 | Boutos |
| 2003/0199806 A1 | 10/2003 | Kieval |
| 2003/0204206 A1 | 10/2003 | Padua et al. |
| 2004/0010303 A1 | 1/2004 | Bolea et al. |
| 2004/0019364 A1 | 1/2004 | Kieval et al. |
| 2004/0039417 A1 | 2/2004 | Soykan et al. |
| 2004/0044393 A1 | 3/2004 | Yarden et al. |
| 2004/0054384 A1 | 3/2004 | Nachum |
| 2004/0064090 A1 | 4/2004 | Keren et al. |
| 2004/0106954 A1* | 6/2004 | Whitehurst et al. ............ 607/3 |
| 2004/0106976 A1 | 6/2004 | Bailey et al. |
| 2004/0111006 A1 | 6/2004 | Alferness |
| 2004/0133240 A1 | 7/2004 | Adams et al. |
| 2004/0162590 A1 | 8/2004 | Whitehurst et al. |
| 2004/0193092 A1 | 9/2004 | Deal |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0090867 A1 | 4/2005 | Lapanashvili et al. |
| 2005/0096710 A1 | 5/2005 | Kieval |
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0203610 A1 | 9/2005 | Tzeng |
| 2005/0209652 A1 | 9/2005 | Whitehurst |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David et al. |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon et al. |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |

(56) References Cited

U.S. PATENT DOCUMENTS

| | | |
|---|---|---|
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | S.E. |
| 2007/0156198 A1 | 7/2007 | Rossing et al. |
| 2007/0156201 A1 | 7/2007 | Rossing |
| 2007/0167984 A1 | 7/2007 | Kieval et al. |
| 2007/0185542 A1 | 8/2007 | Bolea et al. |
| 2007/0185543 A1 | 8/2007 | Rossing et al. |
| 2007/0196428 A1 | 8/2007 | Glauser et al. |
| 2007/0198064 A1 | 8/2007 | Lapanashvili et al. |
| 2007/0248676 A1 | 10/2007 | Stamler et al. |
| 2007/0248850 A1 | 10/2007 | Heller |
| 2007/0276270 A1 | 11/2007 | Tran |
| 2007/0276442 A1 | 11/2007 | Hagen et al. |
| 2007/0276459 A1 | 11/2007 | Rossing et al. |
| 2007/0282385 A1 | 12/2007 | Rossing et al. |
| 2007/0293927 A1 | 12/2007 | Frank et al. |
| 2008/0004673 A1 | 1/2008 | Rossing et al. |
| 2008/0009916 A1 | 1/2008 | Rossing et al. |
| 2008/0009917 A1 | 1/2008 | Rossing et al. |
| 2008/0021336 A1 | 1/2008 | Dobak |
| 2008/0033501 A1 | 2/2008 | Gross |
| 2008/0046016 A1 | 2/2008 | Ben-David et al. |
| 2008/0046054 A1 | 2/2008 | Hjelle et al. |
| 2008/0051767 A1 | 2/2008 | Rossing et al. |
| 2008/0058872 A1 | 3/2008 | Brockway et al. |
| 2008/0071363 A1 | 3/2008 | Tuval et al. |
| 2008/0082137 A1 | 4/2008 | Kieval et al. |
| 2008/0097540 A1 | 4/2008 | Bolea et al. |
| 2008/0119898 A1 | 5/2008 | Ben-David et al. |
| 2008/0119911 A1 | 5/2008 | Rosero |
| 2008/0132972 A1 | 6/2008 | Shuros et al. |
| 2008/0140167 A1 | 6/2008 | Hagen et al. |
| 2008/0154349 A1 | 6/2008 | Rossing et al. |
| 2008/0161865 A1 | 7/2008 | Hagen |
| 2008/0161887 A1 | 7/2008 | Hagen |
| 2008/0167690 A1 | 7/2008 | Cody et al. |
| 2008/0167693 A1 | 7/2008 | Kieval et al. |
| 2008/0167694 A1 | 7/2008 | Bolea et al. |
| 2008/0167696 A1 | 7/2008 | Cates et al. |
| 2008/0167699 A1 | 7/2008 | Kieval et al. |
| 2008/0171923 A1 | 7/2008 | Bolea et al. |
| 2008/0172101 A1 | 7/2008 | Bolea et al. |
| 2008/0172104 A1 | 7/2008 | Kieval et al. |
| 2008/0177364 A1 | 7/2008 | Bolea et al. |
| 2008/0195174 A1 | 8/2008 | Walker et al. |
| 2008/0215117 A1 | 9/2008 | Gross |
| 2009/0036975 A1 | 2/2009 | Ward et al. |
| 2009/0062874 A1 | 3/2009 | Tracey et al. |
| 2009/0198097 A1 | 8/2009 | Gross |
| 2009/0198308 A1 | 8/2009 | Gross et al. |
| 2009/0204170 A1 | 8/2009 | Hastings et al. |
| 2009/0228078 A1 | 9/2009 | Zhang et al. |
| 2009/0234418 A1* | 9/2009 | Kieval et al. ............. 607/44 |
| 2010/0010556 A1 | 1/2010 | Zhao et al. |
| 2010/0076247 A1 | 3/2010 | Zilbershlag et al. |
| 2010/0094373 A1 | 4/2010 | Sharma |
| 2010/0211131 A1 | 8/2010 | Williams et al. |
| 2010/0305392 A1 | 12/2010 | Gross et al. |

FOREIGN PATENT DOCUMENTS

| | | |
|---|---|---|
| WO | WO-9926530 A1 | 6/1999 |
| WO | WO-0002501 A1 | 1/2000 |
| WO | WO-0226314 | 4/2002 |
| WO | WO-03076008 A1 | 9/2003 |
| WO | WO-03082080 A2 | 10/2003 |
| WO | WO-03082403 A2 | 10/2003 |
| WO | WO-2004014456 A2 | 2/2004 |
| WO | WO-2004073484 A2 | 9/2004 |
| WO | WO-2005/065771 A1 | 7/2005 |
| WO | WO-2005084389 A2 | 9/2005 |
| WO | WO-2005097256 A2 | 10/2005 |
| WO | WO-2006012033 A2 | 2/2006 |
| WO | WO-2006012050 A2 | 2/2006 |
| WO | WO-2006032902 A1 | 3/2006 |
| WO | WO-2006041664 A2 | 4/2006 |
| WO | WO-2006064503 A2 | 6/2006 |
| WO | WO-2006/098928 A1 | 9/2006 |
| WO | WO-2006094273 A2 | 9/2006 |
| WO | WO-2006123346 A2 | 11/2006 |
| WO | WO-2006125163 A2 | 11/2006 |
| WO | WO-2007013065 A2 | 2/2007 |
| WO | WO-2007047152 A2 | 4/2007 |
| WO | WO-2007064895 A2 | 6/2007 |
| WO | WO-2007106533 A1 | 9/2007 |
| WO | WO-2007113818 A2 | 10/2007 |
| WO | WO-2007113833 A2 | 10/2007 |
| WO | WO-2007114860 A2 | 10/2007 |
| WO | WO-2007118090 A2 | 10/2007 |
| WO | WO-2007136850 A2 | 11/2007 |
| WO | WO-2007136851 A2 | 11/2007 |
| WO | WO-200803998 A2 | 4/2008 |
| WO | WO-2008083120 A2 | 7/2008 |
| WO | WO-2008083235 A2 | 7/2008 |
| WO | WO-2008100390 A1 | 8/2008 |
| WO | WO-2009/017647 A1 | 2/2009 |
| WO | WO-2009095918 A2 | 8/2009 |
| WO | WO-2009095920 A2 | 8/2009 |

OTHER PUBLICATIONS

Baudrie, V., et al., Optimal frequency ranges for extracting information on cardiovascular autonomic control from the blood pressure and pulse interval spectrograms in mice, AJP-Regul Integr Comp Physiol o vol. 292 o Feb. 2007.

Frost, M.C., et al., Preparation and characterization of implantable sensors with nitric oxide release coatings, Microchemical Journal 74 (2003), pp. 277-288.

Hayashida, H., et al., Comparison of Neurogenic Contraction and Relaxation in Canine Corpus Cavernosum and Penile Artery and Vein, Jpn. J. Pharmacol. 72, pp. 231-240 (1996).

Kugiyama, K., et al., Nitric Oxide Activity Is Deficient in Spasm Arteries of Patients With Coronary Spastic Angina, Circulation. 1996; 94:266-272, 1996 American Heart Association, Inc.

Laitinen, T., et al., Sympathovagal balance is major determinant of short-term blood pressure variability in healthy subjects, 1999 the American Physiological Society, 0363-6135/99, pp. 1245-1253.

Lasso 2515 Variable Circular Mapping Catheter, Biosense Webster, a Johnson & Johnson Company, Online Catalog.

Lewis, M.E., et al., Vagus nerve stimulation decreases left ventricular contractility in vivo in the human and pig heart, Journal of Physiology (2001), 534.2, pp. 547-552.

Malpas, S.C., Neural influences on cardiovascular variability: possibilities and pitfalls, 2002 the American Physiological Society, vol. 282, pp. 6-20.

Matheny, R.G., et al., Vagus nerve stimulation as a method to temporarily slow or arrest the heart, Ann Thorac Surg. Jun. 1997;63(6 Suppl):S28-9.

Paulus, W.T., Beneficial Effects of Nitric Oxide on Cardiac Diastolic Function: 'The Flip Side of the Coin, Heart Failure Reviews, 5, pp. 337-344, 2000, Kluwer Academic Publishers.

Sherman, A.J., et al., Blockade of Nitric Oxide Synthesis Reduces Myocardial Oxygen Consumption In Vivo, Circulation. 1997;95:1328-1334, 1997 American Heart Association, Inc.

(56) References Cited

OTHER PUBLICATIONS

Shin, J.H., et al., Improving the biocompatibility of in vivo sensors via nitric oxide release, The Royal Society of Chemistry 2006, Analyst, 2006, 131, pp. 609-615.
Zhao, G, et al., Loss of Nitric Oxide Production in the Coronary Circulation After the Development of Dilated Cardiomyopathy: A Specific Defect in the Neural Regulation of Coronary Blood Flow, Experimental Pharmacology and Physiology (1996) 23, 715-721.
Schoenfisch, M.H., Improving the Thromboresistivity of Chemical Sensors via Nitric Oxide Release: Fabrication and in Vivo Evaluation of NO-Releasing Oxygen-Sensing Catheters, Analytical Chemistry, vol. 72, No. 6, pp. 1119-1126, Mar. 15, 2000.
International Search Report and Written Opinion dated May 12, 2009 for PCT/IL09/00115.
Preliminary Report on Patentability dated Aug. 12, 2010 for PCT/IL09/00115.
International Search Report and Written Opinion dated Jul. 13, 2009 for PCT/IL09/00117.
Preliminary Report on Patentability dated Aug. 12, 2010 for PCT/IL09/00117.
Sulzer IntraTherapeutics Inc. manufactures the IntraCoil® Self-Expanding Peripheral Stent (IntraCoil® Stent) which is described as a flexible coil-shaped metallic device that is used in the femoral and popliteal arteries in the leg to hold open areas that were blocked by atherosclerotic disease. (Jun. 28, 2002).
CardioMEMS Inc. manufactures the EndoSure® Wireless AAA Pressure Measurement System which is composed of two components: a miniaturized wireless implantable sensor and an external electronics module. The external electronics module is described as wirelessly communicating with the sensors to deliver patient data. The wireless sensors are described as being powered by RF energy transmitted from an external electronics module and transmitting real-time data without batteries. (Nov. 11, 2005).
Cheetah Medical Inc. manufactures the Cheetah Reliant which is described as providing continuous tracking of cardiac output and other parameters of cardiac function such as ventricular ejection time and heart rate. (Jan. 23, 2008).
"Heart rate variability" by Task Force of the European Society of Cardiology and the North American Society of Pacing and Electrophysiology European Heart Journal (1996) 17 354-381.
"Heart rate and vasomotor control during exercise" by Vallais Proceedings of the 29th Annual International Conference of the IEEE EMBS Cité Internationale Lyon France Aug. 23-26, 2007.
"Endogenous and exogenous nitric oxide protect against intracoronary thrombosis and reocclusion after thrombolysis" by Sheng-Kun Yao Circulation. 1995;92:1005-1010.
"Effects of chronic baroreceptor stimulation on the autonomic cardiovascular regulation in patients with drug-resistant arterial hypertension" by Wustmann Hypertension 2009;54;530-536.
Web page relating to EndoSure® Wireless AAA Pressure Measurement System, manufactured by CardioMEMS, Inc.(downloaded from: <http://www.cardiomems.com/content.asp?display= medical+ mb&expand=ess>, Nov. 30, 2010.
Office Action dated Nov. 18, 2009 for U.S. Appl. No. 12/023,900.
"The unequal influences of the left and right vagi on the control of the heart and pulmonary artery in the rattlesnake, *Crotalus durissus*," Taylor, The Journal of Experimental Biology, 212, 145-151, Aug. 2008.
"Coronary vascular sympathetic beta-receptor innervation." Hamilton, American Journal of Physiology, vol. 230, No. 6, Jun. 1976.
U.S. Office Action dated Aug. 9, 2011, for U.S. Appl. No. 12/023,896.
Office Action dated Mar. 15, 2012 issued in U.S. Appl. No. 12/792,227.
International Search Report and Written Opinion dated Dec. 19, 2011 issued on Applicant's PCT/IL2011/00636.
Office Action dated Mar. 13, 2012 issued on U.S. Appl. No. 12/023,896.
Supplementary European Search Report dated Dec. 14, 2012 in connection with European Patent Application No. 06766171.
An Office Action dated Jun. 19, 2012, which issued during the prosecution of U.S. Appl. No. 11/995,904.
An Office Action dated Jul. 18, 2012, which issued during the prosecution of U.S. Appl. No. 13/210,778.
An Office Action dated Aug. 29, 2012, which issued during the prosecution of U.S. Appl. No. 12/792,227.
An International Search Report and a Written Opinion both dated Jul. 5, 2012 which issued on during the prosecution of Applicant's PCT/IL11/00952.
An Office Action dated Oct. 2, 2012, which issued during the prosecution of U.S. Appl. No. 12/851,214.
An Office Action dated Sep. 18, 2012, which issued during the prosecution of U.S. Appl. No. 12/023,896.
An English Translation of an Office Action dated Oct. 8, 2012, which issued during the prosecution of Chinese Patent Application No. 200980111617.8.
Office Action dated Apr. 25, 2013 issued during the prosecution of corresponding U.S. Appl. No. 11/995,904.
Office Action dated May 10, 2013 issued during the prosecution of corresponding U.S. Appl. No. 12/023,896.
Office Action dated Apr. 5, 2013 issued during the prosecution of U.S. Appl. No. 12/792,227.

\* cited by examiner

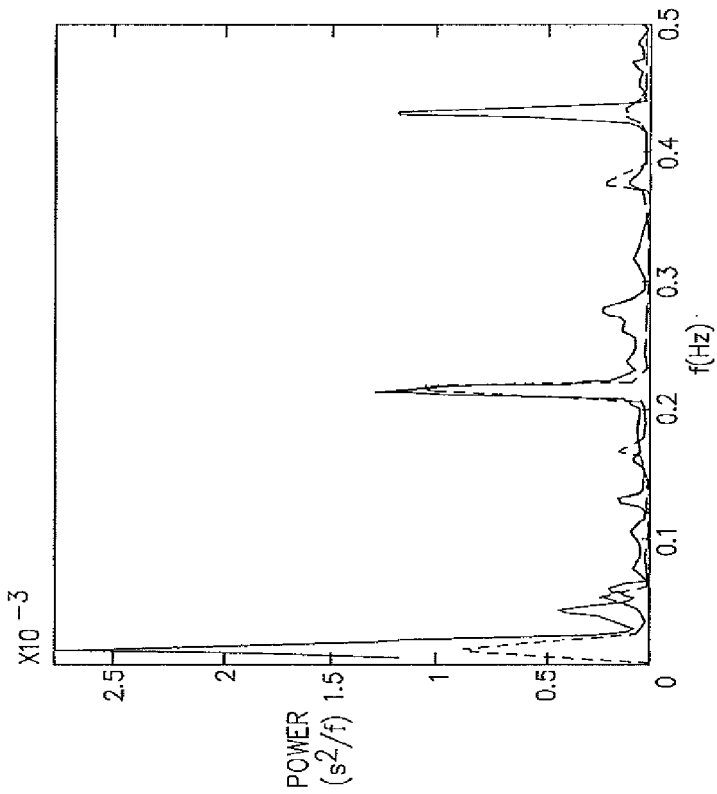
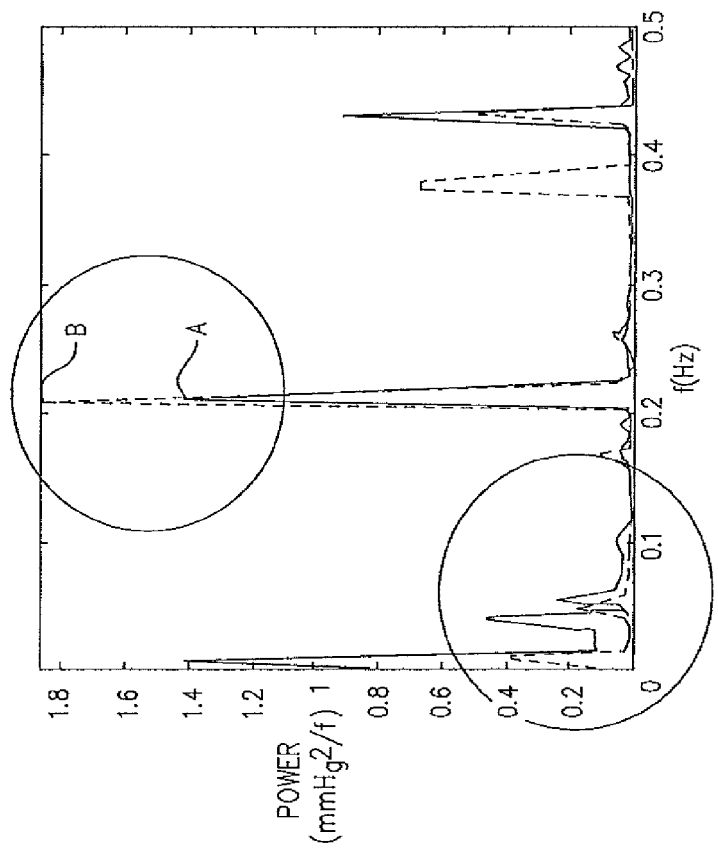

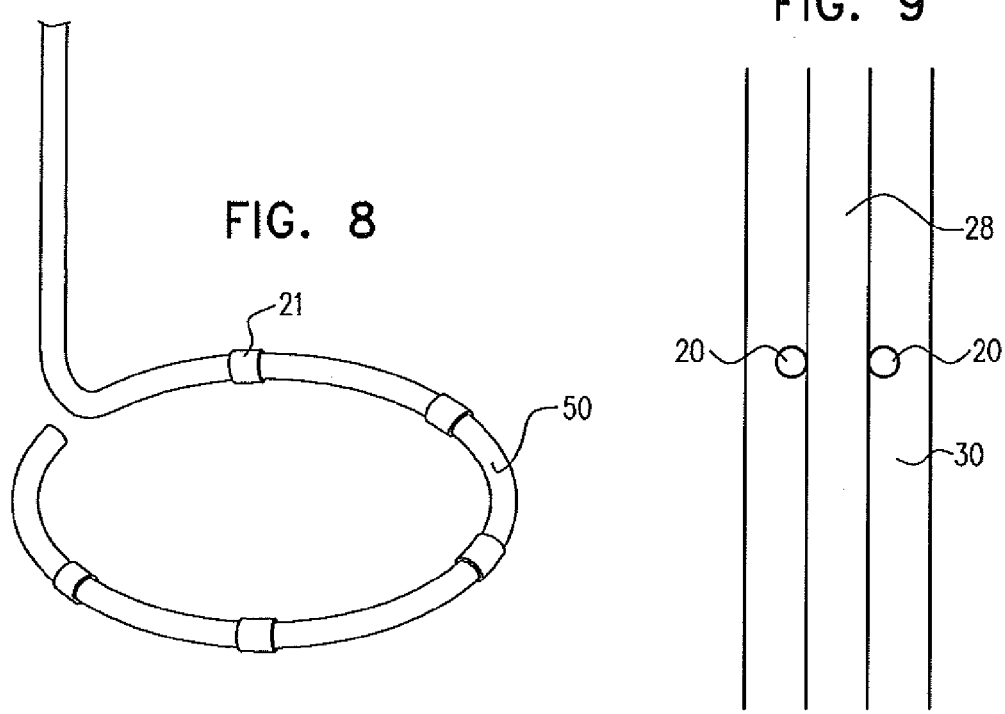
FIG. 8
FIG. 9
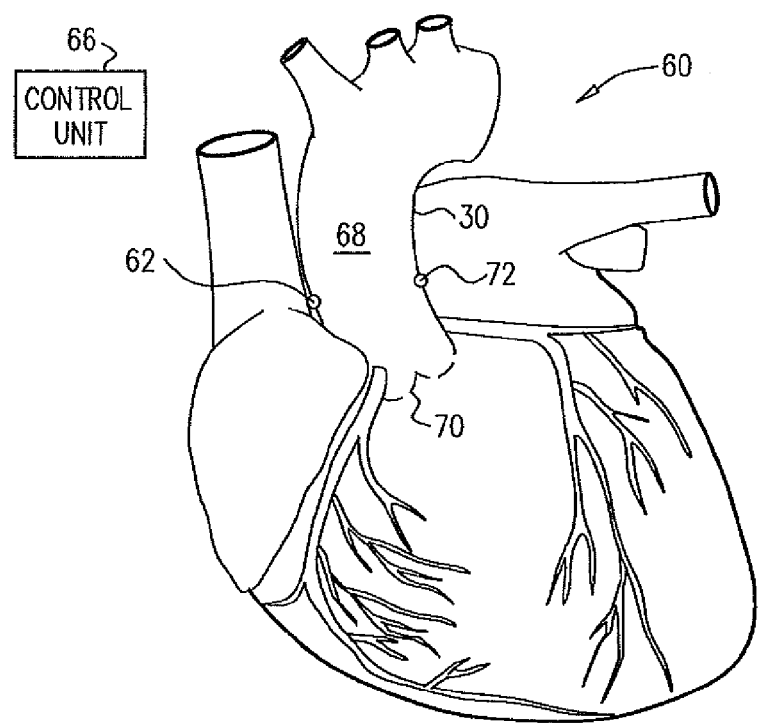
FIG. 10

THORACIC AORTA AND VAGUS NERVE STIMULATION

CROSS-REFERENCES TO RELATED APPLICATIONS

The present application is a continuation-in-part of U.S. Ser. No. 12/792,227 to Gross, filed Jun. 2, 2010, entitled "Thoracic aorta and vagus nerve stimulation," which is a continuation-in part of PCT Application PCT/IL2009/000117 to Gross, filed Jan. 29, 2009, entitled "Intra-aortic electric counterpulsation," which claims the benefit of and is a continuation-in-part of U.S. patent application Ser. No. 12/023,896 to Gross, filed Jan. 31, 2008, entitled "Intra-aortic electric counterpulsation," and claims the benefit of (a) U.S. Provisional Patent Application 61/183,319 to Reisner, filed Jun. 2, 2009, entitled "Thoracic aorta and vagus nerve stimulation," and (b) U.S. Provisional Patent Application 61/331,453 to Dagan, filed May 5, 2010, entitled "Thoracic aorta and vagus nerve stimulation."

The present application is a continuation-in-part of U.S. patent application Ser. No. 12/851,214 to Gross, filed Aug. 5, 2010, entitled "Enhancing perfusion by contracting." All of the above-referenced applications are incorporated herein by reference.

FIELD OF EMBODIMENTS OF THE INVENTION

Some applications of the present invention generally relate to implanted medical apparatus. Specifically, some applications of the present invention relate to apparatus and methods for treating congestive heart failure, diastolic heart failure, hypertension, and/or other conditions.

BACKGROUND

Heart failure is a condition in which a problem with the structure or function of the heart impairs its ability to supply sufficient blood flow to meet the body's needs. The condition impairs quality of life and is a leading cause of hospitalizations and mortality in the western world. Treatment of heart failure is typically aimed at removal of precipitating causes, prevention of deterioration in cardiac function, and control of congestive state.

Hypertension, or chronic high blood pressure, is an extremely prevalent medical condition, which can lead to strokes, heart attacks, and heart failure. There are a variety of treatments that are available for treating hypertension, including lifestyle changes, and medication.

SUMMARY OF EMBODIMENTS

For some applications of the invention a subject suffering from congestive heart failure, diastolic heart failure, hypertension, and/or another condition is identified. The subject is treated by implanting an electrode on the subject's vagus nerve at a vagal site that is between (a) the vagal bifurcation with the thoracic cardiac branch, and (b) the thoracic vagal branching into the esophageal plexus. Alternatively or additionally, an electrode is implanted in the vicinity of (i.e., inside, within the wall of, or outside of) the subject's aorta, at an aortic site that is between the bifurcations of the aorta with the first and fifth intercostal arteries. The subject is treated by driving a current into the electrode implantation site. The effects of driving the current into the implantation site typically include ventricular and aortic pressure reduction, an increase in aortic compliance, a decrease in sympathetic tone, and/or an increase in parasympathetic tone. These effects are typically advantageous in treating heart failure.

For some applications of the present invention, a sensing electrode is implanted in the vicinity of a non-coronary blood vessel of a subject, for example, in the vicinity of an artery, such as the subject's aorta. The sensing electrode detects an electrical parameter of the blood vessel (e.g., the aorta), and a control unit receives the detected parameter and generates an output in response to the detected parameter.

For some applications, the electrode is implanted at a site that is between 20 mm and 50 mm downstream from an aortic valve of the subject.

The electrical parameter that the sensing electrode detects is typically indicative of the subject's cardiac cycle. Thus, for some applications, cardiac-cycle-derivation functionality of the control unit detects the subject's cardiac cycle, and/or a timing parameter of the subject's blood pressure by analyzing the detected parameter. Typically, treatment functionality of the control unit generates an output, responsively to the detected parameter. For example, the treatment functionality may generate an electrical stimulus (e.g., to stimulate a blood vessel of the subject) in response to the detected parameter. Or, the treatment functionality may generate a mechanical stimulus (e.g., a pressure change at the subject's aorta for causing counterpulsation, or afterload reduction), responsively to the detected parameter. For some applications, the treatment functionality generates the mechanical stimulus using a pressure applicator, such as an intra-aortic balloon.

For some applications, the sensing electrode is placed at a first location in the vicinity of a non-coronary blood vessel of the subject, and the control unit generates an output that has an effect at (or in the vicinity of) the first location. For example, the sensing electrode may be placed on an artery that supplies the subject's penis, such as the internal pudendal artery. In response to the detected parameter, the control unit drives an electrode (e.g., the sensing electrode or a different electrode) to drive a current into the internal pudendal artery. Alternatively or additionally, the sensing electrode is placed at a first location in the vicinity of a first non-coronary blood vessel of the subject, and the control unit generates an output that has an effect at a second location within the subject's body (e.g., a location in the vicinity of a second non-coronary blood vessel). For example, the sensing electrode may be placed on the subject's aorta, and in response to the detected parameter, the control unit drives an electrode to drive a current into the subject's internal pudendal artery.

For some applications, the control unit drives a current into the aorta in response to the detected parameter. For some applications, the control unit drives the current in coordination with the subject's cardiac cycle. For example, the subject's cardiac cycle may be determined by analyzing the detected parameter, as described hereinabove. Alternatively, the cardiac cycle is detected using an ECG, and/or by taking impedance measurements, for example, using the Cheetah Reliant, described hereinabove and/or similar technology. For example, in response to detecting systole of the subject, the control unit may dilate the aorta by increasing nitric oxide (NO) secretion by the wall of the aorta by driving the current. Alternatively or additionally, in response to detecting diastole of the subject, the control unit enhances constriction of the aorta by driving the current.

For some applications of the present invention, two, or more electrodes are implanted in a vicinity of an aorta of a subject. A control unit peristaltically pumps blood through the aorta by sequentially dilating portions of the aorta by facilitating nitric oxide production by the aorta by driving a current into the aorta via the electrodes. For some applications, the control unit peristaltically pumps blood through a different blood vessel of the subject, in the aforementioned manner. For example, the control unit may peristaltically pump blood through any artery, such as a renal artery or a carotid artery, or through a vein of the subject.

For some applications, the control unit receives an indication of the subject's cardiac cycle (e.g., using techniques described herein), and drives the current in coordination with the subject's cardiac cycle. Typically, the control unit peristaltically pumps blood through the aorta during systole of the subject. For some applications, during diastole of the subject, the control unit does not peristaltically pump blood through the aorta, and/or the control unit enhances constriction of the aorta by driving a diastolic current into the aorta via the electrodes.

There is therefore provided, in accordance with some applications of the present invention, a method, including:
identifying a subject as suffering from a condition selected from the group consisting of congestive heart failure, diastolic heart failure, and hypertension; and
in response to the identifying:
placing an electrode on a vagus nerve of the subject at a vagal site that is between (a) a vagal bifurcation with a thoracic cardiac branch of the subject, and (b) thoracic vagal branching into the esophageal plexus of the subject; and
treating the subject by driving a current into the vagal site, via the electrode.

For some applications, placing the electrode at the vagal site includes placing the electrode on a portion of the vagus nerve that is adjacent to a portion of an aorta of the subject that is between first and fifth intercostal arteries of the subject.

For some applications, treating the subject includes reducing ventricular pressure of the subject.

For some applications, treating the subject includes reducing aortic pressure of the subject.

For some applications, treating the subject includes reducing sympathetic tone of the subject.

For some applications, treating the subject includes increasing parasympathetic tone of the subject.

For some applications, treating the subject includes increasing aortic compliance of the subject.

For some applications, the method further includes, in response to the identifying:
placing an electrode on an aorta of the subject at an aortic site that is between first and fifth intercostal arteries of the subject; and
treating the subject by driving a current into the aortic site, via the electrode.

For some applications, treating the subject includes increasing parasympathetic tone of the subject and reducing sympathetic tone of the subject.

For some applications, treating the subject includes reducing a ratio of a low frequency component to a high frequency component of heart rate variability of the subject.

For some applications, the low frequency component is less than 0.05 Hz, and the high frequency component is between 0.15 and 0.35 Hz.

For some applications, treating the subject includes reducing a ratio of a low frequency component to a high frequency component of heart rate variability of the subject.

For some applications, the low frequency component is less than 0.05 Hz, and the high frequency component is between 0.15 and 0.35 Hz.

There is further provided, in accordance with some applications of the present invention, a method, including:
identifying a subject as suffering from a condition selected from the group consisting of congestive heart failure, diastolic heart failure, and hypertension; and
in response to the identifying:
placing an electrode on an aorta of the subject at an aortic site that is between first and fifth intercostal arteries of the subject; and
treating the subject by driving a current into the aortic site, via the electrode.

For some applications, placing the electrode at the aortic site includes placing the electrode on a portion of the aorta that is adjacent to a portion of a vagus nerve of the subject that is between (a) a vagal bifurcation with a thoracic cardiac branch of the subject, and (b) thoracic vagal branching into the esophageal plexus of the subject.

For some applications, treating the subject includes reducing ventricular pressure of the subject.

For some applications, treating the subject includes reducing aortic pressure of the subject.

For some applications, treating the subject includes reducing sympathetic tone of the subject.

For some applications, treating the subject includes increasing parasympathetic tone of the subject.

For some applications, treating the subject includes increasing aortic compliance of the subject.

For some applications, placing the electrode on the aorta includes assessing a response of the subject to placement of the electrode at a plurality of sites, and implanting the electrode at the aortic site in response to the assessing.

For some applications, treating the subject includes increasing parasympathetic tone of the subject and reducing sympathetic tone of the subject.

For some applications, treating the subject includes reducing a ratio of a low frequency component to a high frequency component of heart rate variability of the subject.

For some applications, the low frequency component is less than 0.05 Hz, and the high frequency component is between 0.15 and 0.35 Hz.

For some applications, treating the subject includes reducing a ratio of a low frequency component to a high frequency component of heart rate variability of the subject.

For some applications, the low frequency component is less than 0.05 Hz, and the high frequency component is between 0.15 and 0.35 Hz.

There is further provided, in accordance with some applications of the present invention, a method for use with one or more non-coronary blood vessels of a subject, and a body of a subject, including:
at a first location in a vicinity of one of the blood vessels, detecting an electric signal that is indicative of electrical activity at the first location due to a cardiac cycle of the subject; and
responsively thereto, generating an output at a location selected from the group consisting of: the first location, and a second location within the subject's body that is different from the first location.

For some applications, the selected location includes the first location, and generating the output includes generating the output at the first location.

For some applications, the selected location includes the second location, and generating the output includes generating the output at the second location.

For some applications, generating the output includes applying pressure to the selected location.

For some applications, the selected location includes an aorta of the subject, and applying the pressure includes counterpulsating the aorta by applying the pressure.

For some applications, the selected location includes an aorta of the subject, and applying the pressure includes reducing afterload of the subject by applying the pressure.

For some applications, generating the output includes driving a current into the selected location.

For some applications, the method further includes identifying the subject as suffering from erectile dysfunction, the selected location includes an artery of the subject that supplies a penis of the subject, and applying the electrical stimulation to the selected location includes, responsively to identifying the subject as suffering from the erectile dysfunction, treating the erectile dysfunction of the subject.

For some applications, detecting the signal includes detecting the signal at an aorta of the subject.

For some applications, detecting the signal includes detecting the signal at the artery that supplies the penis.

There is additionally provided, in accordance with some applications of the present invention, apparatus for use with one or more non-coronary blood vessels of a subject, and a body of a subject, including:

an electrode configured to be placed at a first location in a vicinity of one of the blood vessels, and to detect an electrical signal of the blood vessel;

cardiac-cycle-derivation functionality configured to derive from the signal a current phase of a cardiac cycle of the subject; and treatment functionality configured, responsively to the derived phase, to generate an output at a location selected from the group consisting of: the first location, and a second location within the subject's body that is different from the first location.

For some applications, the apparatus further includes a pressure-applicator, and the treatment functionality is configured to generate the output by causing the pressure applicator to apply pressure to the selected location.

There is further provided, in accordance with some applications of the present invention, apparatus, including:

an electrode configured to be placed in contact with an artery of a subject;

a control unit configured to drive the electrode to perform a function with respect to the artery, the function selected from the group consisting of: driving a current into the artery, and sensing an electrical parameter of the artery; and a transmitter configured to be placed in a vein of the subject that is in a vicinity of the artery, the transmitter being wiredly connected to the control unit, and the control unit being configured to drive the electrode by wirelessly transmitting a signal via the transmitter.

For some applications, the control unit is configured to be subcutaneously implanted inside the subject.

For some applications, the transmitter includes a coil that defines a plane, and the coil is configured to be placed inside the subject's vein such that the plane defined by the coil is at an angle of more than 10 degrees from a plane that is perpendicular to a local longitudinal axis of the vein.

For some applications, the apparatus further includes a coil support structure, the coil being coupled to the support structure such that the support structure is configured to place the coil inside the subject's vein such that the plane defined by the coil is at the angle of more than 10 degrees from the plane that is perpendicular to the local longitudinal axis of the vein.

For some applications, the transmitter is configured to be placed in a subclavian vein of the subject, and the electrode is configured to be placed in contact with an aorta of the subject.

For some applications, the electrode is configured to be placed in contact with an aortic site that is between first and fifth intercostal arteries of the subject.

For some applications, the transmitter is configured to be placed in the vein such that the transmitter is at a distance of less than 20 mm from the electrode.

For some applications, the transmitter is configured to be placed in the vein such that the transmitter is at a distance of less than 5 mm from the electrode.

There is additionally provided, in accordance with some applications of the present invention, a method, including:

placing an electrode in contact with an artery of a subject;

placing in a vein of the subject that is in a vicinity of the artery, a transmitter that is wiredly connected to a control unit; and using the control unit, driving the electrode to perform a function with respect to the artery, the function selected from the group consisting of: driving a current into the artery, and sensing an electrical parameter of the artery, the driving being performed by the control unit wirelessly transmitting a signal via the transmitter.

For some applications, placing the transmitter inside the vein includes placing the transmitter inside a subclavian vein of the subject, and placing the electrode in contact with the artery includes placing the electrode in contact with an aorta of the subject.

For some applications, placing the electrode in contact with aorta includes placing the electrode in contact with an aortic site that is between first and fifth intercostal arteries of the subject.

For some applications, placing the electrode in contact with the aortic site includes placing the electrode in contact with a portion of the aorta that is adjacent to a portion of a vagus nerve of the subject that is between (a) a vagal bifurcation with a thoracic cardiac branch of the subject, and (b) thoracic vagal branching into the esophageal plexus of the subject.

For some applications, driving the electrode to perform the function with respect to the artery includes reducing ventricular pressure of the subject by driving a current into the aortic site via the electrode.

For some applications, driving the electrode to perform the function with respect to the artery includes reducing aortic pressure of the subject by driving a current into the aortic site via the electrode.

For some applications, driving the electrode to perform the function with respect to the artery includes reducing sympathetic tone of the subject by driving a current into the aortic site via the electrode.

For some applications, driving the electrode to perform the function with respect to the artery includes increasing parasympathetic tone of the subject by driving a current into the aortic site via the electrode.

For some applications, driving the electrode to perform the function with respect to the artery includes reducing sympathetic tone and increasing parasympathetic tone of the subject by driving a current into the aortic site via the electrode.

For some applications, driving the electrode to perform the function with respect to the artery includes increasing aortic compliance of the subject by driving a current into the aortic site via the electrode.

For some applications, placing the electrode in contact with the aorta includes assessing a response of the subject to placement of the electrode at a plurality of sites, and implanting the electrode at the aortic site in response to the assessing.

For some applications, driving the electrode to perform the function with respect to the artery includes reducing a ratio of a low frequency component to a high frequency component of heart rate variability of the subject by driving a current into the aortic site via the electrode.

For some applications, the low frequency component is less than 0.05 Hz, and the high frequency component is between 0.15 and 0.35 Hz.

For some applications, driving the electrode to perform the function with respect to the artery includes reducing a ratio of a low frequency component to a high frequency component of blood pressure variability of the subject by driving a current into the aortic site via the electrode.

For some applications, the low frequency component is less than 0.05 Hz, and the high frequency component is between 0.15 and 0.35 Hz.

There is further provided, in accordance with some applications of the present invention, a method, including receiving power at a transmitter that is disposed in a vein of a subject, and transmitting the power from the transmitter to an electrode that is disposed in an artery of the subject that is in the vicinity of the vein.

The present invention will be more fully understood from the following detailed description of embodiments thereof, taken together with the drawings, in which:

BRIEF DESCRIPTION OF THE DRAWINGS

FIG. 6 is a graph showing the effect of stimulating an aortic site of a pig on blood pressure variability of the pig, in accordance with some applications of the present invention;

FIG. 7 is a graph showing the effect of stimulating an aortic site of a pig on heart rate variability of the pig, in accordance with some applications of the present invention;

FIGS. 8 and 9 are schematic illustrations of electrode configurations that are used, in accordance with some applications of the present invention;

FIG. 10 is a schematic illustration of an electrode implanted in a non-cardiac site in a vicinity of a subject's aorta, in accordance with some applications of the present invention;

DETAILED DESCRIPTION OF EMBODIMENTS

Figure 1A:
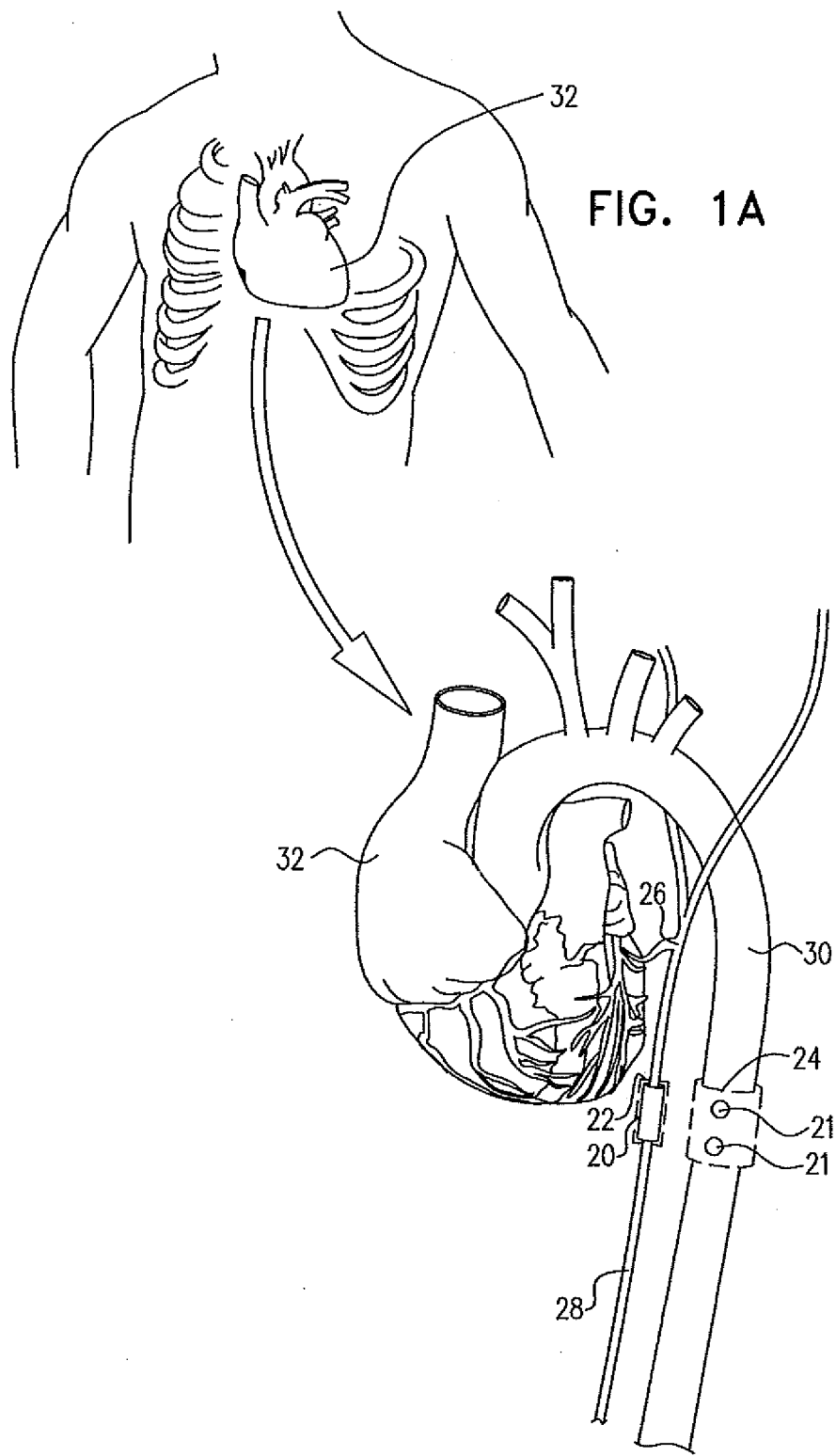
FIGS. 1A-B are schematic illustrations of electrode implantation sites, in accordance with some applications of the present invention.
Figure 1B:
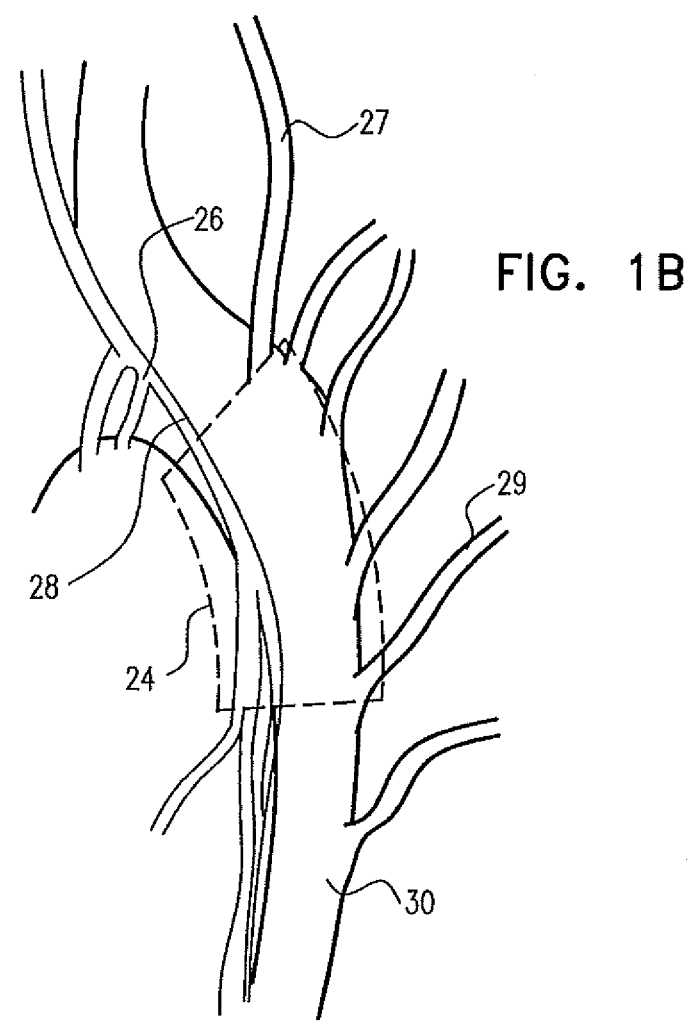

Reference is now made to FIGS. 1A-B, which are schematic illustrations of a vagal site 22 and an aortic site 24 of a subject, in accordance with some applications of the present invention. For some applications, at least one vagal electrode 20 and at least one aortic electrode 21 are implanted, respectively, at vagal site 22 and aortic site 24. In FIG. 1A, vagus nerve 28 is shown separated from aorta 30 for illustrative purposes, although typically the vagus nerve is disposed adjacently to the aorta at aortic site 24, as shown in FIG. 1B.

For some applications of the invention, a subject suffering from congestive heart failure, diastolic heart failure, and/or hypertension is identified. The subject is treated by implanting an electrode on the subject's vagus nerve at vagal site 22 that is between (a) vagal bifurcation 26 with thoracic cardiac branch, and (b) the thoracic vagal branching into the esophageal plexus. Alternatively or additionally, one or more aortic electrodes 21 are implanted in the vicinity of (i.e., inside, outside, or within the wall of) the subject's aorta 30, at aortic site 24 that is between the bifurcations of the descending thoracic aorta with the first and fifth intercostal arteries 27 and 29. For some applications, aortic electrode 21 is implanted in the vicinity of a portion of the aorta that is adjacent to vagal site 22. For some applications, vagal electrode 20 is implanted on a portion of the vagus nerve that is adjacent to aortic site 24. The subject is treated by driving a current into one or more of the electrode implantation sites. The effects of driving the current into the implantation site typically include ventricular and aortic pressure reduction, an increase in aortic compliance, a decrease in sympathetic tone, an increase in parasympathetic tone, an increase in ejection fraction, a reduction in heart rate, a reduction in left ventricular wall stress, a reduction in left ventricular myocardial oxygen consumption, and/or a reduction in arrhythmia. For example, in experiments conducted by the inventors of the present application, patients that had ECG signals that included two QRS complexes in each cardiac cycle were identified. The patients' arrhythmia was at least partially treated by stimulating the patients in accordance with the techniques described herein.

For some applications, an electrode is implanted inside a vein in the vicinity of vagal site 22. For example, the electrode may be implanted in the vena cava, the innominate vein, the subclavian vein, and/or the left or right internal jugular vein. A current is driven via the intravenously implanted electrode in order to stimulate the vagal site, in accordance with the techniques described herein. Alternatively or additionally, the electrode is implanted inside an artery of the subject in the vicinity of the vagal site other than (or in addition to) the aorta, such as the pulmonary artery and/or the carotid artery, and a current is driven via the electrode in order to stimulate the vagal site.

Typically, the lowering of the subject's blood pressure is achieved by driving the current into one or both of the implantation sites, without causing a substantial change in the subject's heart rate. For some applications, there is no substantial effect on the heart rate, because the current is driven into a site that is further from the CNS than the thoracic cardiac bifurcation 26, and therefore does not have a substantial effect on nerves that directly innervate the subject's heart 32. (For some applications, stimulating the vagus nerve distally to bifurcation 26 also has a heart rate lowering effect, but it is hypothesized by the inventors that this effect is mediated through central controls rather than direct efferent stimulation of the heart.) Typically, the lowering of the subject's blood pressure is achieved due to physiological responses that are in addition to any effects on the firing rate of the subject's baroreceptors, due to the applied current. Further typically, vagal electrode 20 and/or aortic electrodes 21 stimulate at least non-baroreceptor vagal terminals of vagal nerve 28.

For some applications, aortic electrodes 21 are disposed inside the aorta (i.e., electrodes 21 are intravascular electrodes). Alternatively or additionally, the electrodes are disposed in a wall of the aorta. Further alternatively or additionally, vagal electrode 20 is a cuff-electrode (or a different design) that is placed around, or in contact with, the vagus nerve. For some applications, electrode 20 and/or electrodes 21 are chronically implanted at sites 22 and/or 24.

For some applications, the current is driven into the electrode implantation site in coordination with the subject's cardiac cycle and/or respiratory cycle. For example, the subject's ECG may be detected, and the current may be driven into the electrode implantation site responsively to the detection of the QRS complex. alternatively or additionally, the subject's blood pressure may be measured and the current may be driven responsively thereto. Alternatively, the current is driven independently of the subject's cardiac cycle and/or respiratory cycle.

For some applications, driving current into aortic site 24, via electrodes 21, dilates the aorta by increasing nitric oxide (NO) secretion by the wall of the aorta, and/or by increasing the secretion of another vasodilation mediator from the wall of the aorta. For some applications, driving current into aortic site 24, via electrodes 21, dilates the aorta by stimulating efferent nerve ending. For some applications, driving current into aortic site 24, via electrodes 21, dilates the aorta by direct electrical hyperpolarization of the vascular smooth muscle. For some applications, the current has a frequency of between 5 Hz and 50 Hz. For some applications, the current has an amplitude of between 1 mA and 15 mA, e.g., between 2 mA and 3 mA. For some applications, a current having two pulses to eight pulses, e.g., three pulses to five pulses, per cardiac cycle, is driven into the aorta to dilate the aorta. In accordance with respective applications, the current is delivered continuously or intermittently. The current may thus be applied, for example: (a) as an endless train of pulses, (b) during scheduled non-contiguous daily stimulation periods, or (c) during each of at least 24 consecutive hours.

For some applications, driving current into vagal site 22, via electrode 20 stimulates parasympathetic nerve endings and elicits a parasympathetic response. For some applications, driving the current into the vagal site stimulates sympathetic nerve endings, and inhibits sympathetic signaling. For some applications, driving current into aortic site 24, via electrodes 21, has a similar effect on the vagus nerve (i.e., a vagal response), due to the proximity of aortic site 24 to vagal site 22, and/or due to vagal nerve endings that are located at the aortic site. For some applications, driving current into the aortic site generates an aortic response, as described hereinabove, in addition to generating the aforementioned vagal response.

For some applications, vagal site 22 is mechanically stimulated, for example, by mechanically stimulating the vagus nerve at the vagal site, and/or by mechanically stimulating aortic site 24, such that the vagal site also becomes stimulated. For some applications, the vagal site is stimulated using piezoelectric actuator terminals, an electrical motor, and/or an electroactive polymer actuator. For some applications, a balloon is placed in the vicinity of the vagal site, and is actuated to mechanically stimulate the vagus nerve using an external pump.

Figure 2:
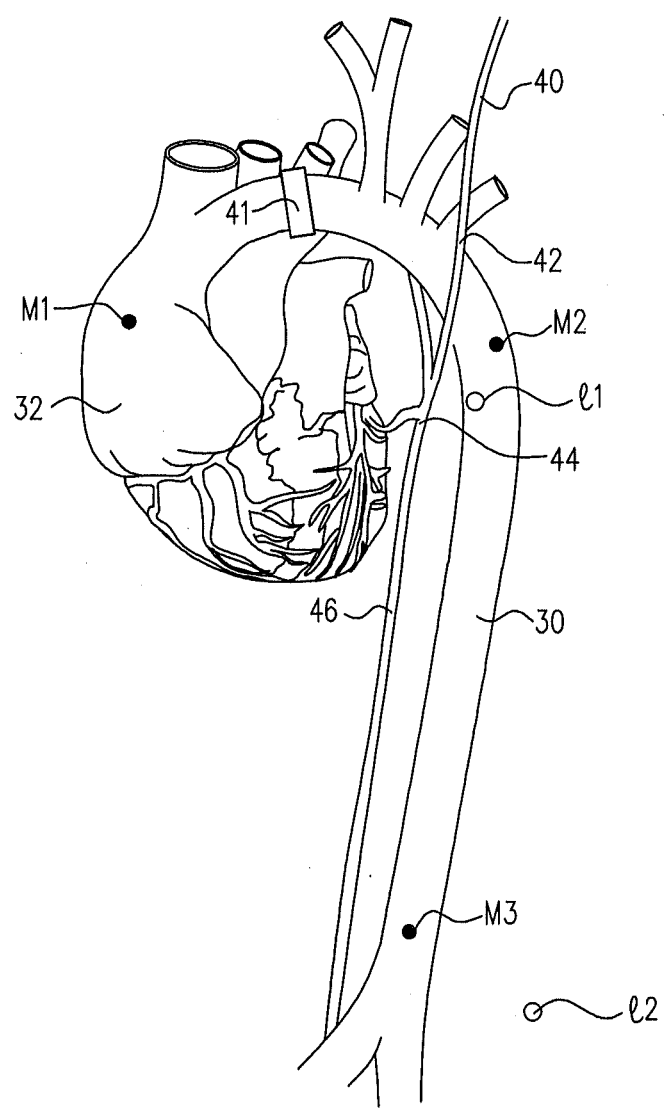
FIG. 2 is a schematic illustration of an experimental setup of an experiment conducted in accordance with some applications of the present invention.

Reference is now made to FIG. 2, which is a schematic illustration of an experimental setup of an experiment conducted in accordance with some applications of the present invention. Cuff electrodes were placed around a pig's vagus nerve at the following four locations:

(1) cervical location 40;
(2) proximal thoracic location 42 which is proximal to (i.e., closer to the CNS than) where the vagus has crossed the aorta;
(3) medial thoracic location 44, 1-2 cm below the aortic arch as the vagus nerve runs alongside the descending aorta, and just distal to (i.e., further from the CNS than) the thoracic cardiac branch bifurcation with the vagus nerve; and
(4) distal thoracic location 46, just distal to (i.e., in a downstream direction along the aorta from) the crossing of the azygos vein with the aorta, and approximately 3 cm distal to (i.e., further from the CNS than) the thoracic cardiac branch bifurcation with the vagus nerve.

Reference electrodes e1 and e2 were placed inside the pig's body, as shown in FIG. 2. Three Millar pressure transducers M1, M2, and M3 were placed, respectively, in the left ventricle, the proximal descending aorta and in the abdominal aorta proximal to the iliac bifurcation. A Transonic flow transducer 41 was positioned around the aortic root. Three minutes of continuous electrical stimulation was applied to each of the sites. Respective sites of the pig's vagus were stimulated in accordance with the parameters provided in Table 1.

TABLE 1

| Stimulation parameters | | | | | |
|---|---|---|---|---|---|
| Active pole | Ref. pole | amplitude [mA] | freq [Hz] | pulse width | stimulation duration |
| 46 Distal | e1 | 5 | 50 | 1-1 ms * | 3 min |
| 44 Medial | e1 | 5 | 50 | 1-1 ms | 3 min |
| 42 Proximal | e1 | 5 | 50 | 1-1 ms | 3 min |

TABLE 1-continued

| Stimulation parameters | | | | | |
|---|---|---|---|---|---|
| Active pole | Ref. pole | amplitude [mA] | freq [Hz] | pulse width | stimulation duration |
| 40 Cervical | e2 | 5 | 50 | 1-1 ms | 3 min |

* i.e., a 1 ms positive pulse, followed by a 1 ms symmetric negative pulse

Figure 3:
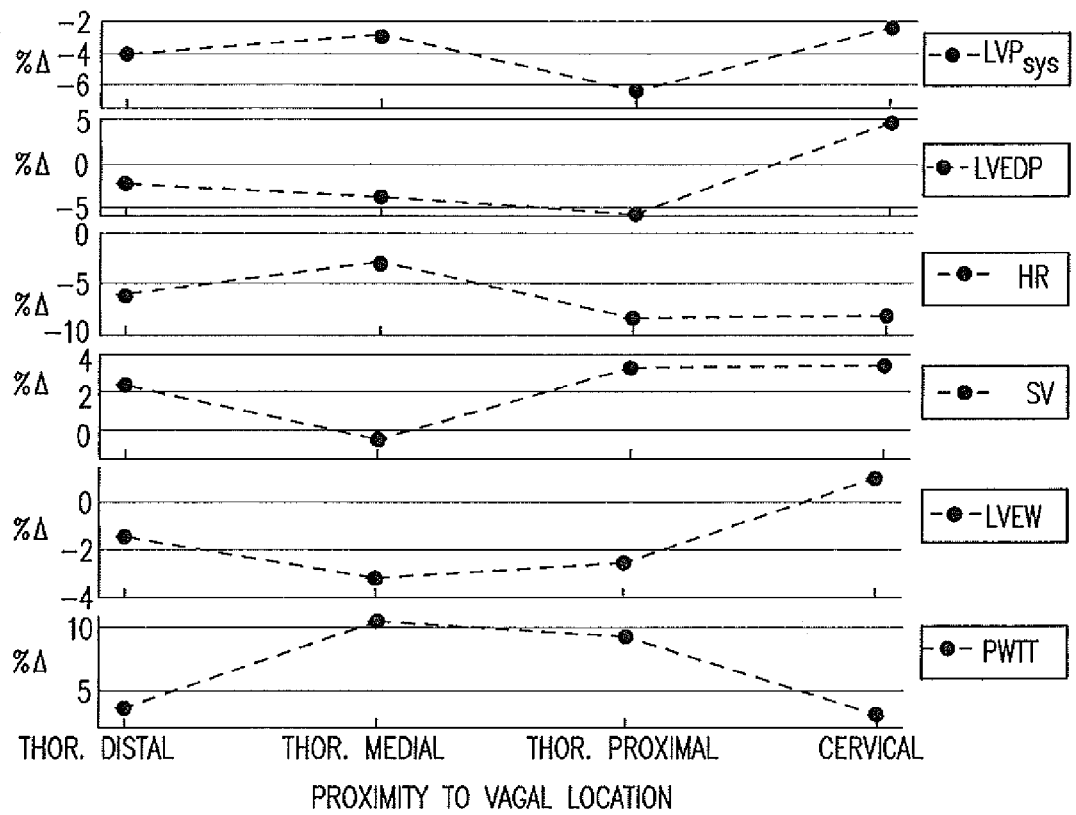
FIG. 3 is a set of graphs showing the results of stimulating a subject's vagus nerve on several physiological parameters of the subject, as determined in the experiment conducted in accordance with some applications of the present invention.

Reference is now made to FIG. 3, which is a set of graphs showing the results of stimulating the pig's vagus on several physiological parameters of pig, as determined in the experiment described with reference to FIG. 2. The following parameters were determined.

LVPsys—Average systolic left ventricular pressure during the ejection phase (aortic valve opening to aortic valve closure).

LVEDP—Left ventricular end diastolic pressure.

HR—Heart rate.

SV—Stroke volume as measured in the aortic root.

LVEW—Left ventricular external work. The integral of the product of left ventricular pressure and aortic flow during ejection phase.

PWTT—Pulse wave travel time between two measuring points along the aorta. PWTT is correlated to the square root of the diameter of the aorta divided by stiffness. Hence, increased PWTT (decreased pulse wave velocity) is associated with decreased aortic wall tonus.

The numeric values shown in the graphs of FIG. 3 represent the average of each parameter, for respective stimulation sites, during the entire stimulation regime. The following observations can be made regarding the graphs shown in FIG. 3:

Electrical stimulation at all locations induced a reduction of average systolic left ventricular pressure during the ejection phase and heart rate. The systolic left ventricular pressure reduction was maximal in the proximal site and minimal in the cervical site.

The left ventricular end diastolic pressure was reduced in the thoracic sites and increased in the cervical site.

Heart rate reduction was maximal in the proximal thoracic and cervical sites.

Stroke volume did not exhibit a clear trend, as the medial thoracic site yielded a slight decrease and the other sites resulted in 2-4% increase.

Left ventricular external work, which is related to cardiac consumption, was lower as a result of stimulation of the thoracic sites and higher while stimulating the cervical site.

Stimulation at all of the sites resulted in an increase in pulse wave travel time (i.e., a decrease in aortic tonus). Stimulation of the proximal and medial sites resulted in the largest pulse delay along the aorta.

Figure 4:
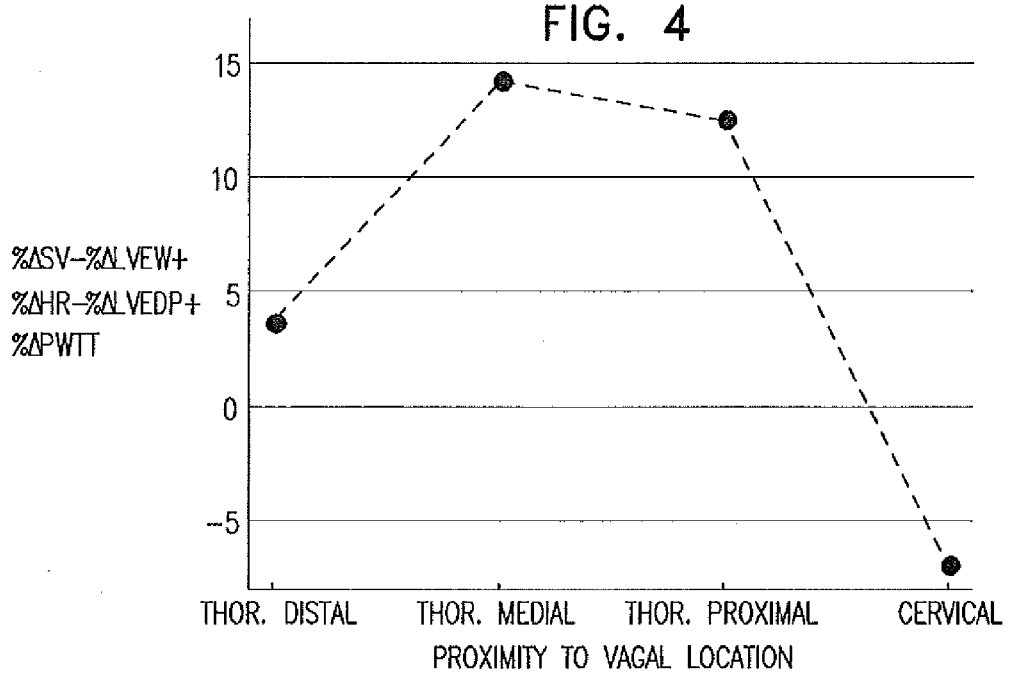
FIG. 4 is a graph showing a composite result of stimulating the subject's vagus nerve, as determined in the experiment conducted in accordance with some applications of the present invention.

Reference is now made to FIG. 4, which is a graph showing a composite result of stimulating the pig's vagus, as determined in this experiment. In order to evaluate each of the stimulation sites with one parameter, a first order scoring function was applied. The percentage change in each of the parameters shown in the graph of FIG. 3 was added to the total score, and its sign was determined according to the presumed beneficial direction. Left ventricular external work and left ventricular end diastolic pressure, which are targeted to be reduced (when treating patients suffering from hypertension, for example), were added with negative signs. Pulse wave travel time and stroke volume were added with positive signs. The heart rate reduction was also assigned a positive score.

The function results are plotted in the graph shown in FIG. 4. It may be observed that the thoracic medial site has the highest score, and all of the thoracic sites achieved positive scores. The cervical vagal site achieved an overall negative score, since, although it had a positive effect on heart rate (i.e., heart rate reduction), its effect on pressure and work reduction was non-beneficial across the entire stimulation regime.

Figure 5:
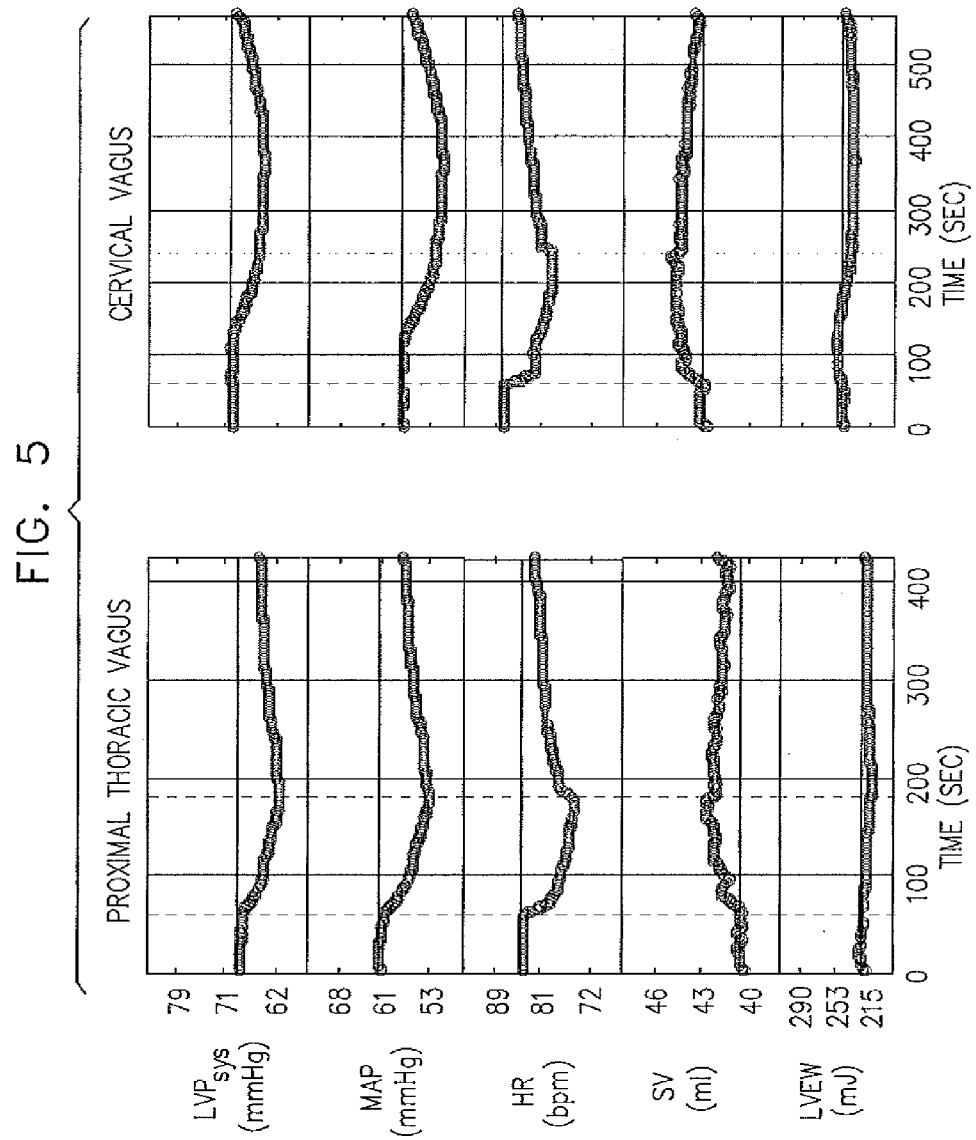
FIG. 5 is a graph showing the dynamic response of a subject to the stimulation of the subject's vagus nerve, as determined in the experiment conducted in accordance with some applications of the present invention.

Reference is now made to FIG. 5, which is a graph showing the dynamic response of the pig to the stimulation of the pig's vagus nerve, as determined in this experiment. The dynamic response to stimulation of the proximal thoracic and the cervical sites is shown in FIG. 5. The beginnings and ends of the stimulation period are marked with dashed vertical lines, at approximately 60 sec and 180 sec on the proximal thoracic vagus graph, and 60 sec and 230 sec on the cervical vagus graph. Heart rate response in both cases was immediate and continued for the duration of the stimulation period. Similarly, there was stroke volume elevation for the duration of the stimulation, due to stimulation at both sites. The pressure and left ventricular external work responses were not similar, however. The proximal thoracic site generated almost immediate pressure and work reduction. In the cervical site, the pressure reduction appeared only late in stimulation (possibly, as a secondary indirect phenomenon), and the left ventricular external work parameter responded with initial increases that were present across most of the stimulation regime.

In view of the results presented herein, it is hypothesized by the inventors of the present application that, as compared to stimulation of the cervical vagus, stimulation of thoracic vagal sites, as described herein, results in (a) a greater overall desired response with respect to ventricular and aortic blood pressure reduction and decreased aortic tonus, and (b) a more rapid response time to the stimulation. The inventors further hypothesize that placing electrodes on an aortic site that is between the first and the fifth intercostal arteries of a human subject, will generate a similar response to the response of the pig to the placement of electrodes at the proximal, medial and distal sites, in the experiment described herein. The inventors additionally hypothesize that placing electrodes on a vagal site that is adjacent to the aforementioned aortic site will also generate a similar response.

The inventors further hypothesize that stimulating a subject's vagus nerve and/or aorta at the sites specified herein is beneficial for treating the subject, such that the subject's (a) ventricular blood pressure, aortic blood pressure, and/or aortic tonus is reduced, without causing (b) a substantial reduction in the subject's heart rate. Conversely, stimulating a subject's vagus nerve and/or aorta at a more proximal site (i.e., at a site along the vagus nerve that is closer to the CNS, and/or at a site along the aorta that is further upstream) may cause a greater reduction in the subject's heart rate and a smaller reduction in the subject's ventricular blood pressure, aortic blood pressure, and/or aortic tonus.

Reference is now made to FIG. 6, which is a graph showing the effect of stimulating an aortic site of a pig on blood pressure variability of the pig, in accordance with some applications of the present invention. Two aortic electrodes were placed inside the pig's aorta at an aortic site as described hereinabove, i.e., between the bifurcations of the descending thoracic aorta with the first and fifth intercostal arteries. To generate the graph shown in FIG. 6, the baseline blood pressure variability of the pig was measured (while the electrodes were not applying current to the aortic site). The baseline blood pressure variability is denoted in the graph by the solid curve. The curve was generated by collecting the baseline data for seven minutes. Subsequently, the electrodes were driven to drive a current into the aortic site having the following parameters: amplitude 10 mA, frequency 125 Hz, and pulses that were 2 ms on, 2 ms off. Blood pressure was measured during the stimulation period. The dotted curve in FIG. 6 shows the blood pressure variability based on seven minutes of the measured blood pressure during the stimulation period.

It may be observed that the effect of the stimulation on the blood pressure variability was to decrease the low frequency components of the blood pressure (those less than 0.15 Hz, e.g., less than 0.05 Hz) and to increase the high frequency components (those in the range of 0.15-0.35 Hz). For example, the frequency component at about 0.21 Hz increases from peak A to peak B, as shown. Thus, the stimulation at the aortic site caused a decrease in the ratio of low frequency components to the high frequency components ("the LF:HF ratio"). In accordance with an article entitled, "Sympathovagal balance is major determinant of short-term blood pressure variability in healthy subjects," by Laitinen, Am J Physiol Heart Circ Physiol 276:1245-1252, 1999, which is incorporated herein by reference, a decrease in the LF:HF ratio is indicative of inhibition of sympathetic activity and/or an increase of parasympathetic activity. This is because the low frequency components of the blood pressure variability are indicative of sympathetic activity, and the high frequency components are indicative of parasympathetic vagal activity. This experiment, therefore, not only shows a decrease in the LF:HF ratio, but also, inhibition of sympathetic activity and increase of parasympathetic activity.

Reference is now made to FIG. 7, which is a graph showing the effect of stimulating an aortic site of a pig on heart rate variability of the pig, in accordance with some applications of the present invention. It is noted that the pig used to generate the results shown in FIG. 7 was a different pig from the pig used to generate the results shown in FIG. 6.

Two aortic electrodes were placed inside the pig's aorta at an aortic site as described hereinabove, i.e., between the bifurcations of the descending thoracic aorta with the first and fifth intercostal arteries. To generate the graph shown in FIG. 7, the baseline heart rate variability of the pig was measured, while the electrodes were not applying current to the aortic site. The baseline heart variability is denoted in the graph by the solid curve. The curve was generated by collecting the baseline data for seven minutes. The electrodes were driven to drive a current into the aortic site having the following parameters: amplitude 10 mA, frequency 125 Hz, and pulses that were 2 ms on, 2 ms off. The heart rate of the pig was measured during the stimulation period. The dotted curve in FIG. 7 shows the heart rate variability based on seven minutes of the measured blood pressure during the stimulation period.

It may be observed that the effect of the stimulation on the heart rate variability was to decrease the low frequency components of the blood pressure (those less than 0.15 Hz, e.g., less than 0.5 Hz). Thus, the stimulation at the aortic site caused a decrease in the ratio of low frequency components to the high frequency components ("the LF:HF ratio"). In accordance with a technique described in "Effects of chronic baroreceptor stimulation on the autonomic cardiovascular regulation in patients with drug-resistant arterial hypertension," by Wustmann, Hypertension 2009; 54; 530-536, which is incorporated herein by reference, a decrease in the LF:HF ratio of heart rate variability is indicative of inhibition of sympathetic activity and/or an increase of parasympathetic vagal activity. In this experiment, an increase in parasympathetic activity is seen.

It is noted that although it may be observed in FIG. 7 that stimulation of the pig caused a decrease in frequency components of the heart rate variability above 0.4 Hz, such components are not indicative of parasympathetic activity. Only the high frequency components up to around 0.35 Hz indicate parasympathetic activity, in accordance with the article, "Heart rate variability," Eur Heart J, Vol. 17, March 1996, and, in particular, FIG. 4 thereof. Although some frequency components in the range of 0.15-0.35 Hz were decreased (e.g., at about 0.23 Hz), the decrease in these frequency components was small relative to the decrease in the low frequency components (e.g., at about 0.02 Hz). Therefore, the overall effect of the stimulation was to cause a decrease in the LF:HF ratio.

In accordance with the results shown in FIGS. 6 and 7, for some applications, a subject suffering from congestive heart failure, diastolic heart failure, and/or hypertension is treated by placing electrodes at an aortic site and/or a vagal site, as described herein. Parasympathetic activity of the subject is increased and/or sympathetic activity of the subject is decreased by driving a current into the site.

Reference is now made to FIG. 8, which is a schematic illustration of an electrode configuration that is used for stimulating an aortic site of a subject, in accordance with some applications of the present invention. For some applications, one or more aortic electrodes 21 are disposed on a loop 50. The loop is transvascularly placed inside the subject's aorta at the aortic site, such that the aortic electrodes contact the intravascular surface of the aorta at the aortic site. When the electrodes have been placed in contact with the intravascular surface of the aorta, current is driven into the aorta via the electrodes, in accordance with the methods described hereinabove. For example, the LASSO 2515 Variable Circular Mapping Catheter, manufactured by Biosense Webster, may be used for loop 50. Typically, the electrode configuration shown in FIG. 8 is used to stimulate the aortic site during an acute treatment of the subject, e.g., during a medical procedure.

Reference is now made to FIG. 9, which is a schematic illustration of an electrode configuration that is used for stimulating vagal and/or aortic sites of a subject, in accordance with some applications of the present invention. For some applications, two electrodes 20 are placed on respective sides of vagus nerve 28, such that the electrodes are in contact with both the vagus nerve and the aorta. For some applications a plurality of electrodes are placed on one or both sides of the vagus nerve, such that each of the electrodes is in contact with both the aorta and the vagus nerve.

For some applications, a subject is anesthetized for the purpose of performing a cardiac intervention and/or a different intervention on the subject. While the subject is in an anesthetized state, it is desirable that the subject has reduced afterload and increased preload relative to the subject's normal levels of afterload and preload. Thus, for some applications, while a subject is in an anesthetized state, the methods described herein are applied to the subject in order to reduce afterload and/or to increase preload of the subject.

Reference is now made to FIG. 10, which is a schematic illustration of apparatus 60, comprising at least one electrode 62 implanted at a non-cardiac site in a vicinity of a subject's aorta 30, in accordance with some applications of the present invention. For some applications, electrode 62 detects an electrical parameter of the subject's aorta, and a control unit 66 receives the detected parameter and generates an output in response to the detected parameter.

For some applications, control unit 66 is disposed inside the subject's body, e.g., in a vicinity of the subject's aorta 30, or remote therefrom, similar to the implanted pulse generator of a standard cardiac pacemaker. Alternatively, the control unit is disposed outside the subject's body.

For some applications, electrode 62 is disposed inside the aorta. Alternatively or additionally, the electrode is disposed in a non-cardiac site in a vicinity of the aorta, and/or in a wall of the aorta. For some applications, electrode 62 is chronically implanted at the site in the vicinity of the aorta. Alternatively the electrode is implanted temporarily, for example, for a period of four weeks or less. For some applications, at least two electrodes 62 are implanted in the subject. One of the electrodes is placed inside the aorta, and another of the electrodes is placed outside the aorta. For some applications, first and second electrodes 62 are placed within the aorta at a longitudinal distance from each other of between 10 mm and 30 mm and/or at a radial distance from each other of less than 10 degrees. For some applications, one or more electrodes 62 are placed in the subject's ascending aorta and one or more electrodes are placed in the subject's aortic arch and/or descending aorta. For some applications, ten or more electrodes, for example 20 electrodes are implanted inside the aorta. Typically, electrode 62 is implanted in a site of the ascending aorta 68 at a site that is between 20 to 50 mm downstream from an aortic valve 70 of the subject. Alternatively, the electrode is placed in the aortic arch, or in the descending aorta.

For some applications, control unit 66 detects the subject's cardiac cycle, and/or a timing parameter of the subject's blood pressure by analyzing the detected parameter. For some applications, the control unit drives a current into the aorta, or into a different blood vessel, in response to the detected parameter. Examples of such detecting and current application are described hereinbelow.

For some applications, the control unit drives the current in coordination with the subject's cardiac cycle. Alternatively, control unit 66 drives a current into the subject's aorta, or a different blood vessel, independently of the subject's cardiac cycle.

For some applications, the control unit drives the current into the aorta via sensing electrode 62. Alternatively or additionally, apparatus 60 comprises one or more additional driving electrodes 72, and the control unit drives the current into the aorta via the driving electrodes. Typically, the placement parameters of the driving electrodes are similar to those described hereinabove, with respect to sensing electrode(s) 62. For some applications, the driving electrodes are oriented to have a surface area of between 3 square mm and 15 square mm, e.g. between 5 square mm and 12 square mm, in contact with tissue of the aorta.

For some applications, control unit 66, by driving a current into the aorta, dilates the aorta by increasing nitric oxide (NO) secretion by the wall of the aorta. Typically, the control unit dilates the aorta in response to detecting an indication of systole of the subject. For some applications, dilating the aorta during systole reduces the left ventricular afterload of the subject, and thereby increases the subject's stroke volume and/or ejection fraction. Alternatively, the aorta may be dilated during systole for a different purpose.

For some applications, the control unit dilates the aorta by configuring the current to have a frequency of between 5 Hz and 20 Hz, e.g., between 10 Hz and 15 Hz. For some applications, the current has an amplitude of between 1 mA and 5 mA, e.g., between 2 mA and 3 mA. For some applications, a current having two pulses to eight pulses, e.g., three pulses to five pulses, per cardiac cycle, is driven into the aorta to dilate the aorta.

For some applications, control unit 66 enhances constriction of the aorta by driving a current into the aorta. For example, the control unit may enhance constriction of the aorta in response to the control unit detecting an indication of diastole of the subject. For some applications, enhancing constriction of the aorta during diastole elevates diastolic blood pressure, thereby increasing coronary perfusion, and/or the supply of blood to organs of the subject's body other than the heart. Alternatively, constriction of the aorta may be enhanced during diastole for a different purpose.

For some applications, the control unit enhances constriction of the aorta by driving a current having a frequency of between 40 Hz and 70 Hz. For some applications, the current has an amplitude of between 5 mA and 20 mA, e.g., between 8 mA and 15 mA. For some applications, a current having ten pulses to twenty pulses, e.g., thirteen pulses to seventeen pulses, per cardiac cycle, is driven into the aorta to enhance constriction of the aorta.

For some applications, control unit 66, (a) in response to detecting systole of the subject, dilates the aorta by increasing nitric oxide (NO) secretion by the wall of the aorta by driving a current into the aorta, and (b) in response to detecting diastole of the subject, enhances constriction of the aorta by driving a current into the aorta. For example, the control unit may dilate the aorta during every systole, and enhance constriction of the aorta during intermittent diastoles. Alternatively, the control unit may dilate the aorta during intermittent systoles, and enhance constriction of the aorta during every diastole. Further alternatively, the control unit may dilate the aorta during every systole, and enhance constriction of the aorta during every diastole. Typically, a suitable protocol is selected based on the medical condition of the subject.

For some applications, a sensing electrode 62 is implanted in the vicinity of a non-coronary blood vessel of the subject that is not the aorta. Alternatively or additionally, as described hereinabove, sensing electrode 62 is implanted in the vicinity of the aorta. The sensing electrode detects an electrical parameter of the blood vessel (e.g., the aorta), and a control unit receives the detected parameter and generates an output in response to the detected parameter. The electrical parameter that the sensing electrode detects is typically indicative of the subject's cardiac cycle. Thus, for some applications, cardiac-cycle-derivation functionality of the control unit derives the subject's cardiac cycle, and/or a timing parameter of the subject's blood pressure by analyzing the detected parameter.

Typically, treatment functionality of the control unit generates an output, responsively to the detected parameter. For example, the treatment functionality may generate an electrical stimulus (e.g., to stimulate a blood vessel of the subject, as described herein) in response to the detected parameter. Or, the treatment functionality may generate a mechanical stimulus (e.g., a pressure change at the subject's aorta for causing counterpulsation, or afterload reduction), responsively to the detected parameter.

For some applications, sensing electrode 62 is placed at a first location in the vicinity of a non-coronary blood vessel of the subject, and the control unit generates an output that has an effect at (or in the vicinity of) the first location. For example, as described hereinabove, the control unit may electrically stimulate the aorta, responsively to sensing at the aorta. Alternatively, the sensing electrode may be placed on an artery that supplies the subject's penis, such as the internal pudendal artery. In response to the detected parameter, the control unit drives an electrode (e.g., the sensing electrode or a different electrode) to drive a current into the internal pudendal artery. Alternatively or additionally, the sensing electrode is placed at a first location in the vicinity of a first non-coronary blood vessel of the subject, and the control unit generates an output that has an effect at a second location within the subject's body (e.g., a location in the vicinity of a second non-coronary blood vessel). For example, the sensing electrode may be placed on the subject's aorta as described hereinabove, and, in response to the detected parameter, the control unit drives an electrode to drive a current into the subject's internal pudendal artery.

Figure 11A:
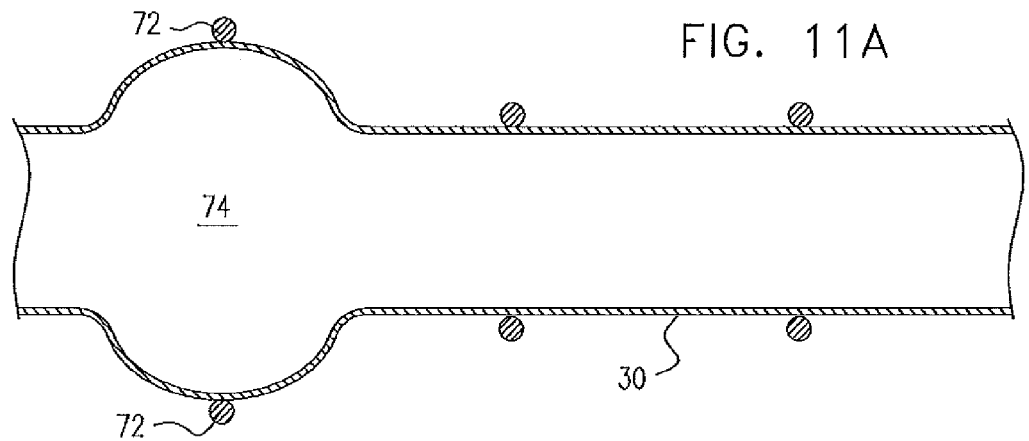
FIGS. 11A-C are schematic illustrations of peristaltic dilation of the aorta, in accordance with some applications of the present invention.
Figure 11B:
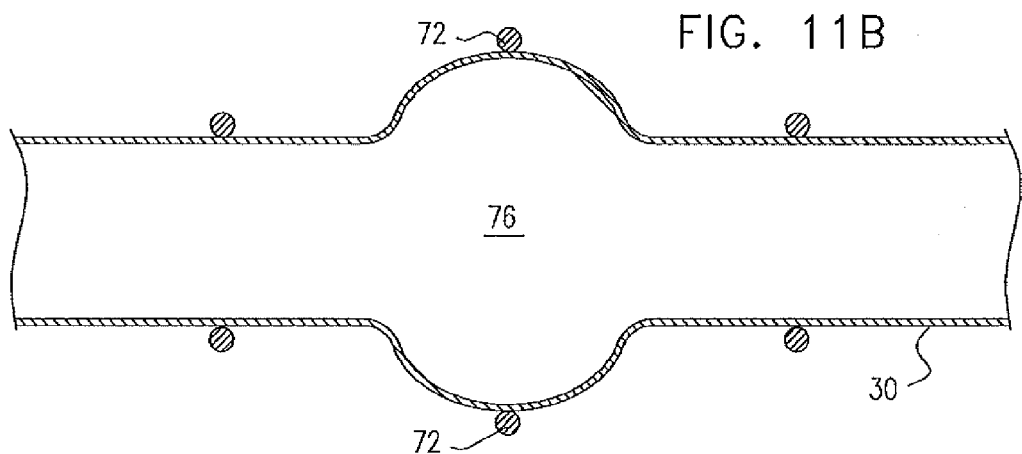
Figure 11C:
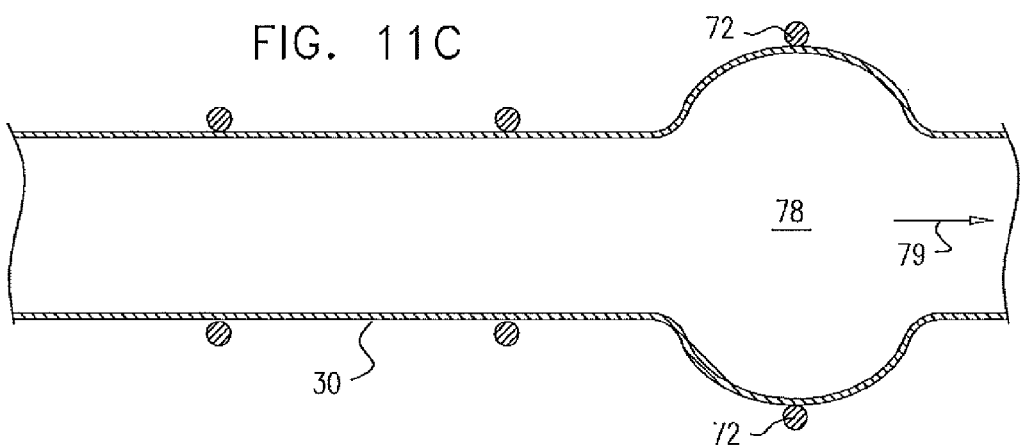

Reference is now made to FIGS. 11A-C, which are schematic illustrations of peristaltic dilation of aorta 30, in accordance with some applications of the present invention. For some applications of the invention, control unit 66 (FIG. 10) peristaltically pumps blood through the aorta by sequentially dilating portions of the aorta by facilitating nitric oxide production by the aorta by driving a current into the aorta via two or more electrodes disposed at respective longitudinal positions on the aorta. Typically, during diastole, control unit 66 causes a region 74 of the aorta to dilate by driving a current through the most-downstream electrodes of electrodes 72 (as shown in FIG. 11A). The current is sequentially driven through the remaining electrodes, causing regions 76 and 78 to dilate (as shown in FIGS. 11B and 11C respectively), and causing blood to flow in an upstream direction, in the direction of arrow 79, to enhance coronary artery perfusion. Alternatively, peristalsis generated as described is used to generate downstream-directed enhanced blood flow.

Although applications are described herein according to which the aorta is peristaltically pumped, the scope of the present application includes applying to any blood vessel in the subject's body, the methods and apparatus for peristaltic pumping that are described herein. For example, the scope of the present invention includes peristaltically pumping blood through a subject's renal artery, carotid artery, or a vein, by peristaltically dilating the blood vessel.

Typically, the parameters of the current for dilating the aorta are as described hereinabove. Typically, the parameters of the electrodes (i.e., the number and spacing of the electrodes) are as described hereinabove. Further typically, the electrodes are configured to induce dilation with a spacing in time of 10 ms to 50 ms. For some applications, the electrodes are disposed longitudinally along the aorta with a longitudinal spacing therebetween of 150%-250% of the local diameter of the aorta and/or of 1-5 cm. The spacing may be maintained, for example, by a housing to which the electrodes are coupled (e.g., a flexible stent) or by sutures or adhesives which couple the electrodes to the aorta. As appropriate for the level of peristaltic flow desired, the time for a peristaltic wave to be generated and to travel from the most downstream to the most upstream electrode (or in the opposite direction) typically ranges from 0.25 second to about 2 seconds.

For some applications, control unit 66 receives an indication of the subject's cardiac cycle (e.g., via sensing electrode 62, which may be placed at the aorta or at a different non-coronary blood vessel, as described hereinabove), and peristaltically pumps blood in the aorta by driving the current in coordination with the subject's cardiac cycle. For some applications, the control unit peristaltically pumps blood through the aorta during systole of the subject. For some applications, a peristaltic wave of constriction of the aorta is generated as well as the peristaltic wave of dilation described hereinabove. The peristaltic wave of constriction is behind the peristaltic wave of dilation, and pushes the blood in the peristaltic wave of dilation. For example, while region 76 of the aorta is dilated (as shown in FIG. 11B), region 74 is constricted (constriction not shown), and subsequently, while region 78 is dilated, region 76 is constricted.

For some applications, during diastole of the subject, control unit 66 (a) does not peristaltically pump blood through the aorta, and/or (b) enhances constriction of the aorta by driving a diastolic current into the aorta via the electrodes. Typically, the parameters of the diastolic current for enhancing constriction of the aorta are as described hereinabove.

For some applications, control unit 66 peristaltically pumps blood proximally during diastole by generating a proximally-directed peristaltic wave of dilation and/or contraction using the techniques described hereinabove.

For some applications, control unit 66 peristaltically dilates the aorta during intermittent or all systoles, and/or enhances constriction of the aorta during intermittent or all diastoles.

Typically, control unit 66 comprises a battery. Alternatively, the control unit is powered wirelessly, e.g., by being irradiated with electromagnetic radiation, and/or ultrasound radiation from outside the subject's body, or by extracting energy from the subject's body. For example, the control unit may be disposed inside the subject's aorta, and configured to extract energy from the flow of blood through the aorta. Alternatively or additionally, the control unit may extract energy from the subject's gastric acid.

Figure 12:
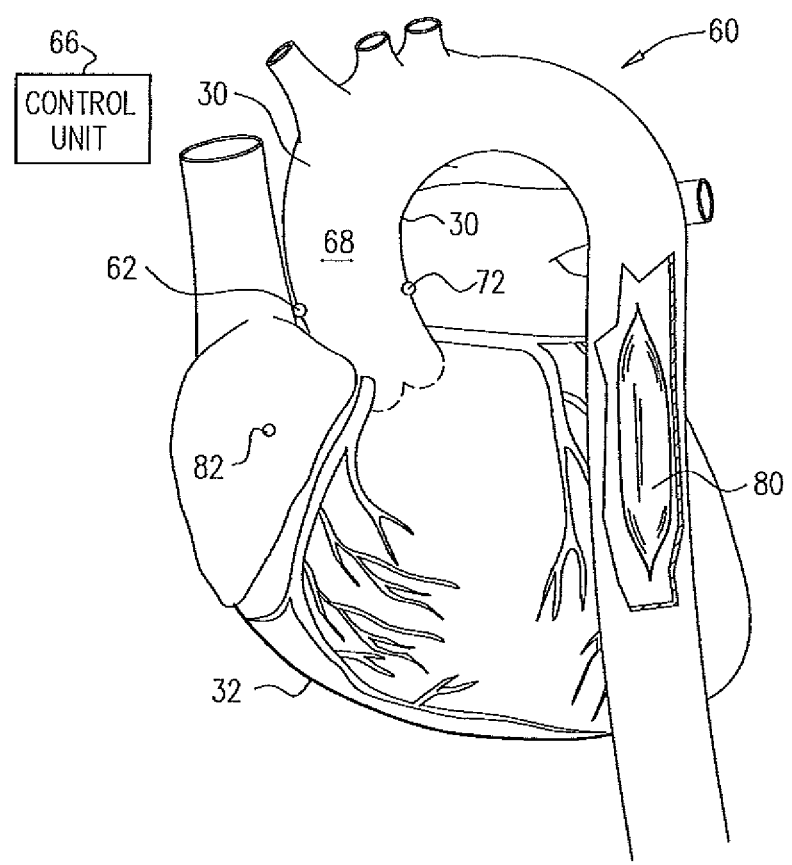
FIG. 12 is a schematic illustration of a control unit configured to generate an output in response to a detected aortic electrical parameter, in accordance with some applications of the present invention.

Reference is now made to FIG. 12, which is a schematic illustration of apparatus 60, in accordance with some applications of the present invention. For such applications, a pressure applicator, such as an intra-aortic balloon pump 80 is implanted in a subject's aorta. Control unit 66 pumps the intra-aortic balloon pump in response to the electrical parameter of the aorta or of a different non-coronary blood vessel that is detected by electrode 62.

For some applications, in addition to, or instead of pump 80, apparatus 60 includes at least one cardiac electrode 82 implanted in a vicinity of the subject's heart 32. Control unit 66 drives a current into the subject's heart, via the cardiac electrode, in response to the electrical parameter of the aorta, or of a different non-coronary blood vessel that is detected by sensing electrode 62. For some applications, the control unit defibrillates or cardioverts the subject's heart by driving the current into the subject's heart, in response to aortic sensing, other non-coronary blood vessel sensing, and/or in response to sensing on the heart.

Figure 13A:
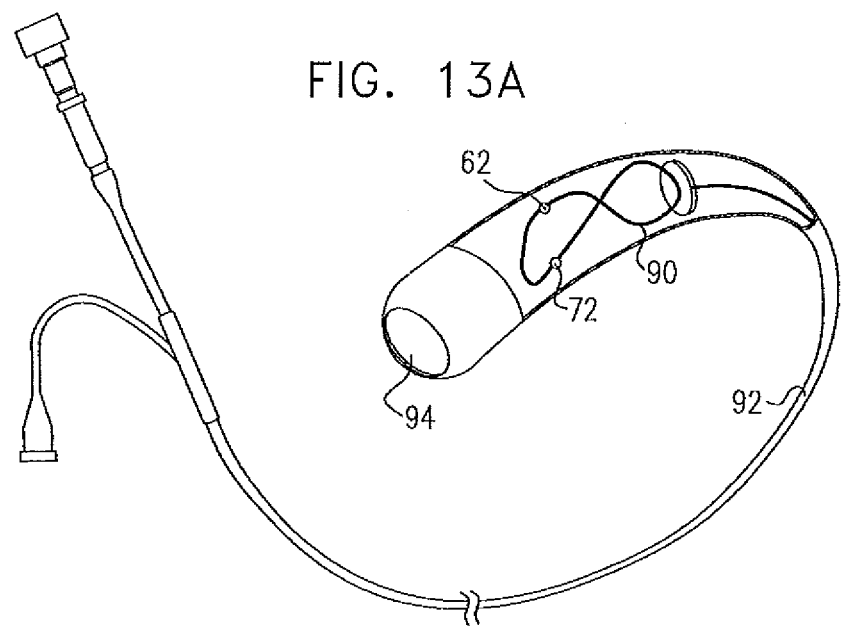
FIGS. 13A-B are schematic illustrations of electrodes disposed on a self-expansible stent, in accordance with some applications of the present invention.
Figure 13B:
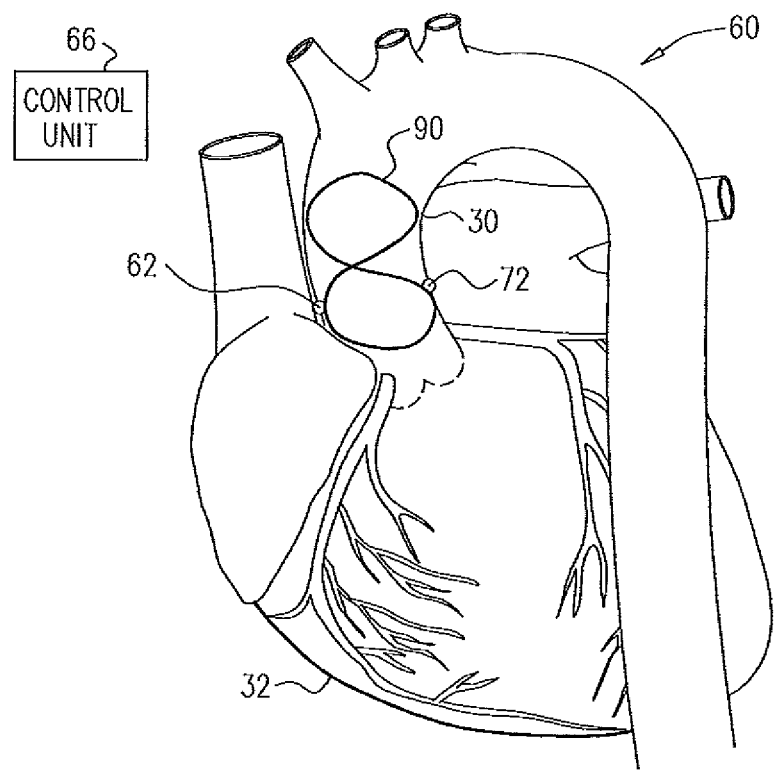

Reference is now made to FIGS. 13A-B, which are schematic illustrations of electrodes 62 and/or 72 disposed on a self-expansible stent 90, in accordance with some applications of the present invention. Typically, the stent is inserted into the subject's aorta 30, via a catheter 92. The stent is in a contracted state when it is inside the catheter, and expands automatically inside the aorta upon exiting the distal end 94 of catheter.

Figure 14A:
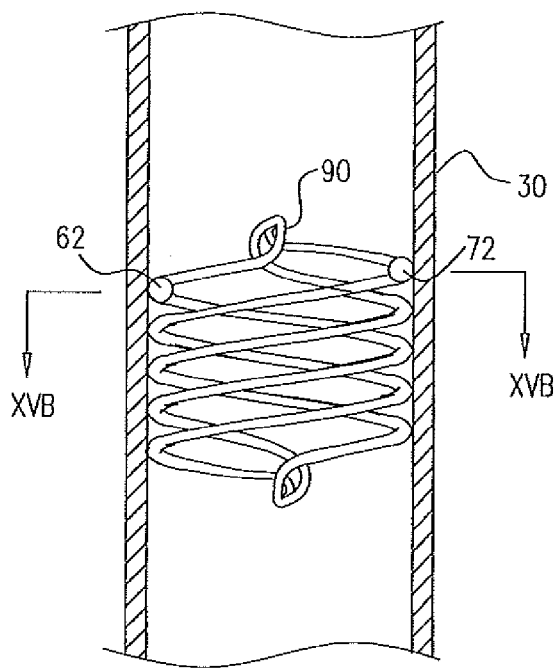
FIGS. 14A-B are schematic illustrations of respective views of a configuration of the self-expansible stent, in accordance with another application of the present invention.
Figure 14B:
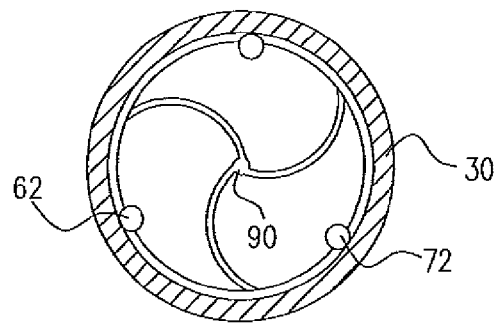

Reference is now made to FIGS. 14A-B, which are schematic illustrations of respective views of a configuration of self-expansible stent 90, in accordance with some applications of the present invention. For some applications, stent 90 (as shown) is shaped as two or more spirals. The spirals are in contracted states inside catheter 92, and are held in place inside aorta 30 by expanding inside aorta 30.

Figure 15A:
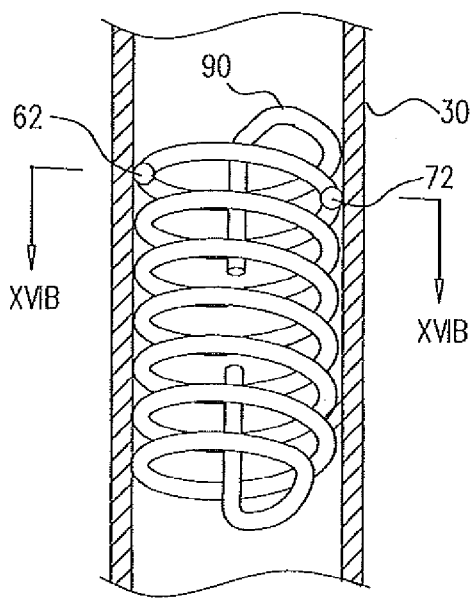
FIGS. 15A-B are schematic illustrations of respective views of an alternative configuration of the self-expansible stent, in accordance with some applications of the present invention.
Figure 15B:
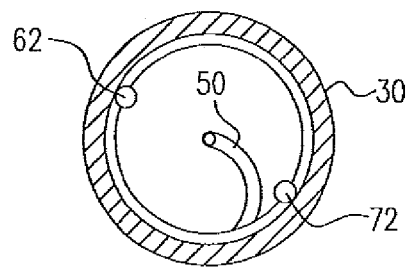

Reference is now made to FIGS. 15A-B, which are schematic illustrations of respective views of an alternative configuration of self-expansible stent 90, in accordance with some applications of the present invention. For some applications, stent 90 (as shown) is shaped as a coil. The coil is in a contracted state inside catheter 92, and is held in place inside aorta 30 by expanding inside aorta 30.

Figure 16A:
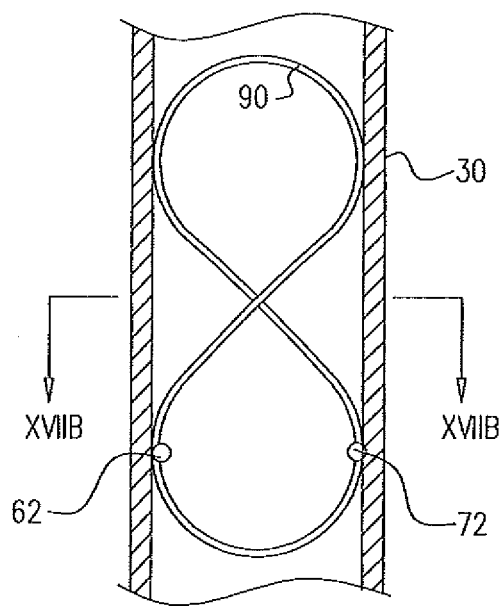
FIGS. 16A-B are schematic illustrations of respective views of a further alternative configuration of the self-expansible stent, in accordance with some applications of the present invention.
Figure 16B:
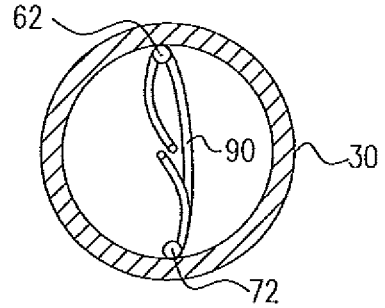

Reference is now made to FIGS. 16A-B, which are schematic illustrations of respective views of a further alternative configuration of self-expansible stent 90, in accordance with some applications of the present invention. For some applications, stent 90 (as shown) is shaped as a figure-of-eight. The figure-of-eight is in a contracted state inside catheter 92, and is held in place inside aorta 30 by expanding inside aorta 30.

Figure 17:
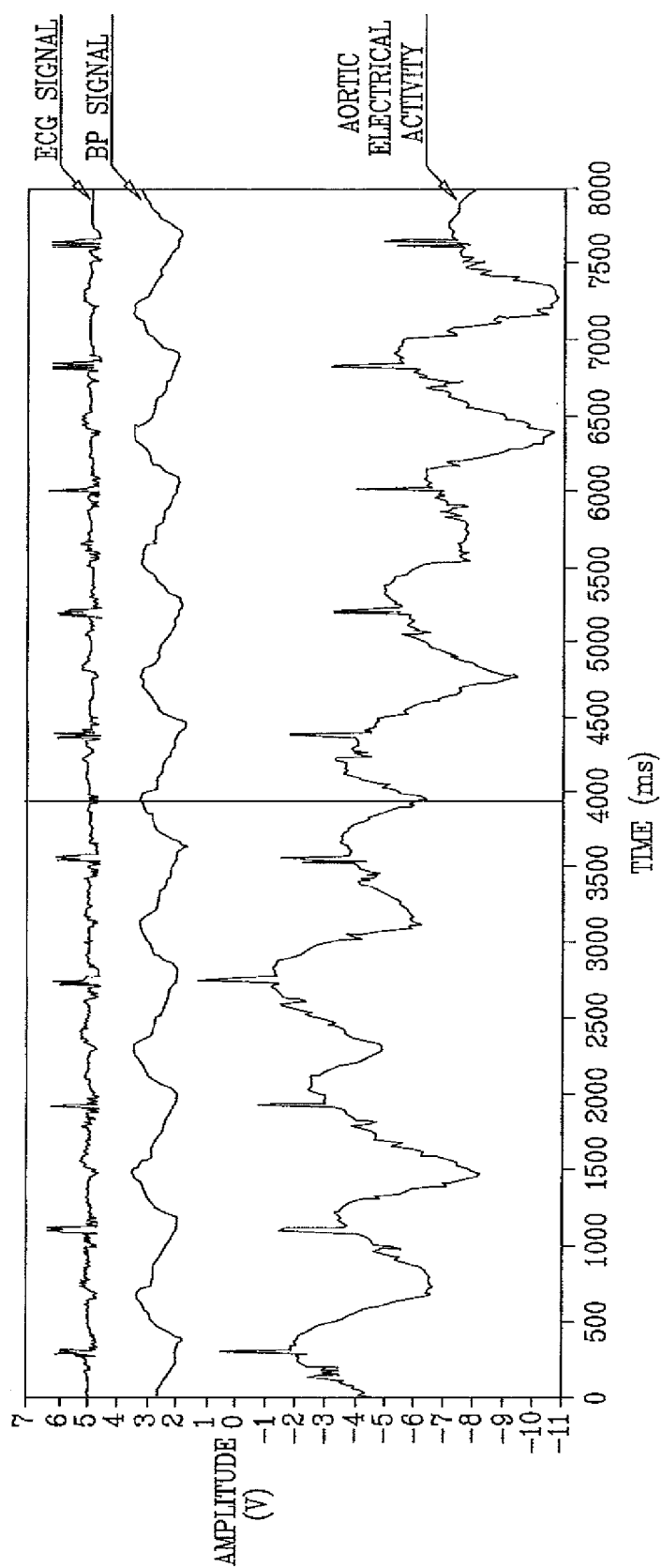
FIG. 17 is a plot of an aortic voltage signal recorded in an aorta of a pig, in an experiment conducted in accordance with some applications of the present invention.

Reference is now made to FIG. 17, which is a graph of aortic electrical activity recorded in an aorta of a pig, in an experiment conducted in accordance with some applications of the present invention. Ten electrodes were placed in an aorta of a pig close to the aortic valve, and the voltage within the aorta was recorded via four of the ten electrodes. The graph shows the variation of the voltage within the aorta plotted against time. In addition, and concurrently, the pig's ECG and blood pressure were measured. The graph additionally shows the concurrent ECG and blood pressure measurements, which were respectively recorded with an external ECG electrode and with an intra-aortic blood pressure sensor.

Based upon the data in FIG. 17 and in other experiments carried out by the inventors, the inventors have identified relationships between the cardiac cycle and the voltage recorded in the aorta. For example:

(1) There is a sharp peak in the aortic voltage about 50-100 ms before the onset of the aortic pressure rise due to systole. For example, at 2000 ms there is an onset of the pressure rise, and about 70 ms before this onset there is a sharp peak in the aortic voltage.

(2) Shortly before the onset of the aortic pressure decline due to diastole, the aortic voltage reaches a minimum. For example, there is a solid vertical line through the graph at about 3950 ms, at which point, the aortic voltage is at a local minimum. At about 4000 ms, diastole begins.

(3) A signal component in the measured aortic voltage corresponds to, and appears quite similar to, the R-wave recorded with an external ECG electrode, shown in the top trace. For example, the spike in the aortic voltage signal at 6000 ms corresponds to the R-wave in the ECG signal at 6000 ms.

Thus, the inventors have found that important mechanical events (onset of aortic pressure rise and aortic pressure decline) and electrical events (the R-wave) can be identified by aortic sensing, and, for some applications, are processed and used to trigger a medical device, such as an intra-aortic balloon pump or a pulse generator. The inventors hypothesize that mechanical and electrical events of other blood vessels that are indicative of the subject's cardiac cycle can be detected by sensing electrical activity of the other blood vessels. For example, a sensing electrode placed in the vicinity of a non-coronary artery that is not the aorta (e.g., the internal pudendal artery) may be used to detect electrical and/or mechanical events of the artery that are indicative of a phase of the subject's cardiac cycle.

Figure 18:
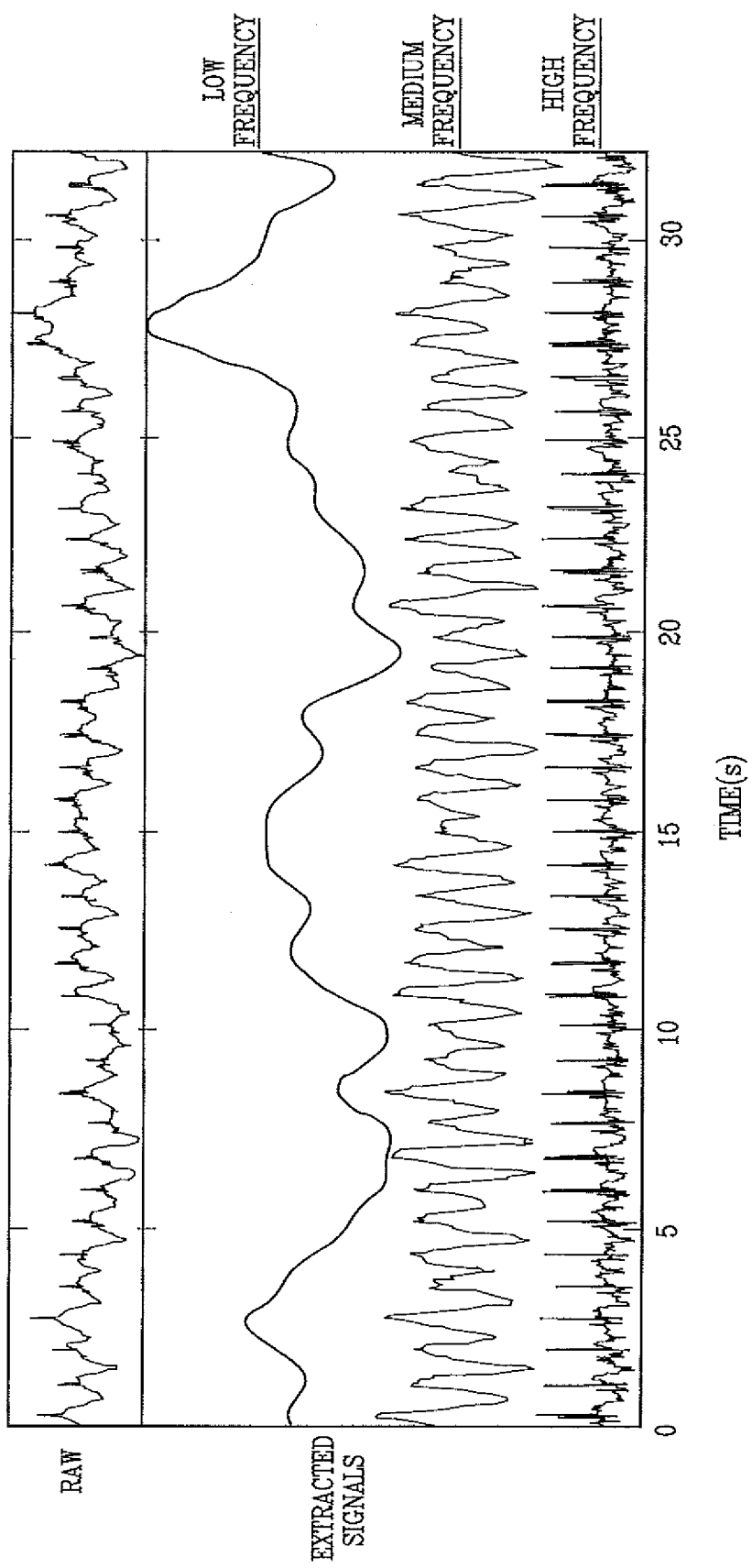
FIG. 18 is a plot showing frequency components of the aortic voltage signal of FIG. 17, as extracted from the raw aortic voltage signal in accordance with some applications of the present invention.

Reference is now made to FIG. 18, which is a plot showing frequency components extracted from the raw aortic voltage signal of FIG. 17, in accordance with some applications of the present invention. The aortic voltage signal was separated into three frequency components, a low-frequency component, a medium-frequency component, and a high-frequency component.

Figure 19:
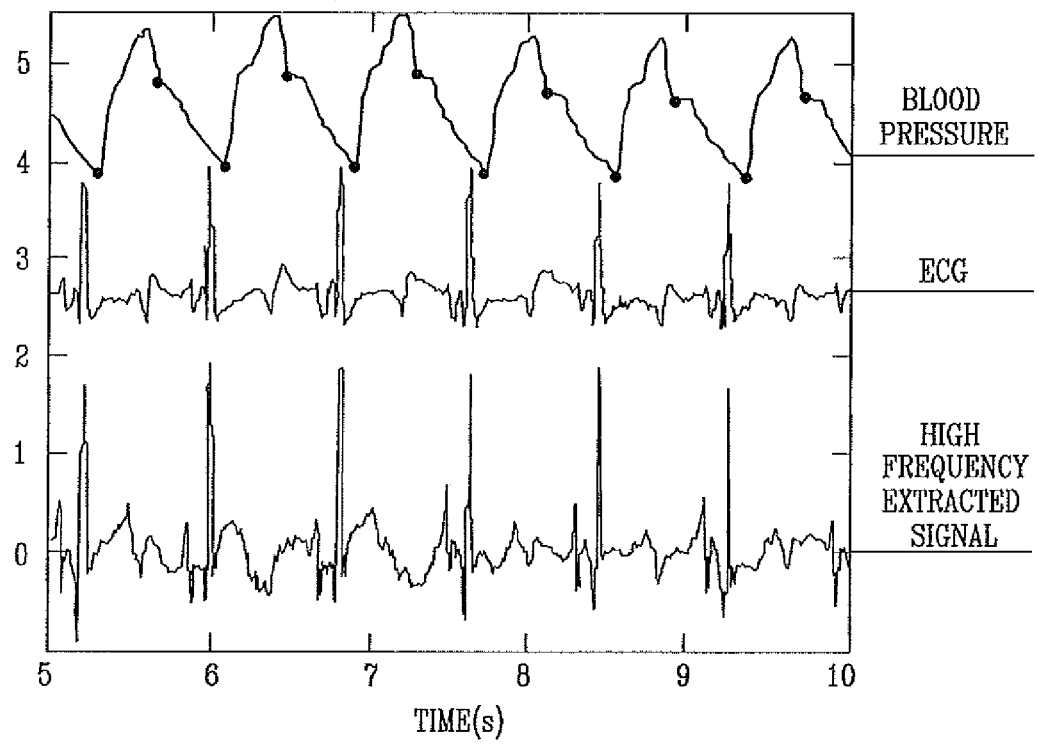
FIG. 19 is a plot comparing a frequency component of the aortic voltage signal of FIG. 17 to the pig's ECG and blood pressure signals, in accordance with some applications of the present invention.

Reference is now made to FIG. 19, which shows the high frequency component of the aortic voltage signal plotted together with an ECG recorded by the external electrode and the recorded blood pressure. It was observed by the inventors that the high frequency component has a similar pattern to the ECG signal, as can be seen in FIG. 19. Furthermore, there is a relationship between the occurrence of systole and diastole (which are indicated by the dots on the blood pressure plot), and the plot of the high frequency signal. As such, for some applications of the invention, an ECG signal of a subject is detected by sensing an electrical parameter in the subject's aorta. For some applications, a subject's ECG signal is detected by sensing electrical activity of another non-coronary blood vessel of the subject. For example, a sensing electrode placed in the vicinity of a non-coronary artery other than the aorta (e.g., the internal pudendal artery) may be used to detect the subject's ECG signal.

Figure 20:
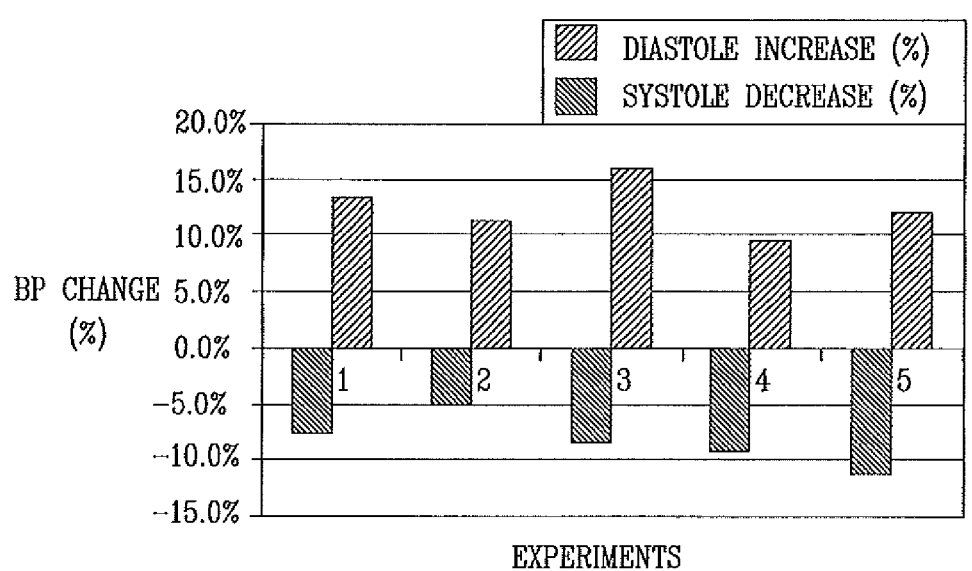
FIG. 20 is a graph showing blood pressure changes measured in five experiments conducted on four pigs, in accordance with some applications of the present invention.

Reference is now made to FIG. 20, which is a graph showing blood pressure changes measured in five experiments conducted on four pigs, in accordance with some applications of the present invention. In each experiment, the pig was opened surgically, and electrodes (having configurations described hereinbelow) were implanted on the aortic wall. In each of the five experiments, currents having respective parameters were driven into the pigs' aortas during systole and diastole. The systolic currents dilated the aorta (thus decreasing systolic aortic blood pressure), by increasing nitric oxide (NO) secretion by the wall of the aorta. The diastolic currents enhanced constriction of the aorta (thus increasing diastolic aortic blood pressure).

The parameters of the electrodes used, and the currents with which the aortas were stimulated in each of the five experiments, were in accordance with Table 2 below. In Table 2, "Type 1" electrodes denotes Pathfinder electrodes manufactured by Cardima (CA) [product no. 01-161003]. "Type 2" electrodes denotes electrodes, which were custom made for the inventors, each of the custom-made electrodes having a length of 13.3 mm to 13.5 mm, having a diameter of 0.52 mm, and being pointed at a distal end thereof. The custom-made electrodes were oriented to have approximately 10 sq mm of surface area in contact with the wall of the aorta and to be at a minimum distance of 10 mm from each other. All of the electrodes were implanted in the ascending aortas of the pigs.

TABLE 2

| Experiment | Electrode | Systolic current | Diastolic current |
| --- | --- | --- | --- |
| 1 | Type 1 | 2 mA monophasic 20 Hz 6 pulses per cardiac cycle | 8 mA monophasic 40 Hz 15 pulses per cardiac cycle |
| 2 | Type 2 | 5 mA monophasic 30 Hz 2 pulses per cardiac cycle | 12 mA monophasic 80 Hz 15 pulses per cardiac cycle |
| 3 | Type 2 | 2 mA monophasic 20 Hz 6 pulses per cardiac cycle | 8 mA monophasic 50 Hz 15 pulses per cardiac cycle |
| 4 (This experiment was performed on the same pig as that of experiment 3) | Type 2 | 2 mA monophasic 12 Hz 4 pulses per cardiac cycle | 7 mA monophasic 50 Hz 16 pulses per cardiac cycle |
| 5 | Type 1 | 1 mA monophasic 20 Hz 6 pulses per cardiac cycle | 10 mA monophasic 60 Hz 4 pulses per cardiac cycle |

The mean decrease in the systolic blood pressure, as a result of the systolic currents, was 8.3±2.3% (mean±standard deviation). The mean increase in diastolic blood pressure, as a result of the diastolic currents, was 12.4±2.5% (mean±standard deviation).

Figure 21:
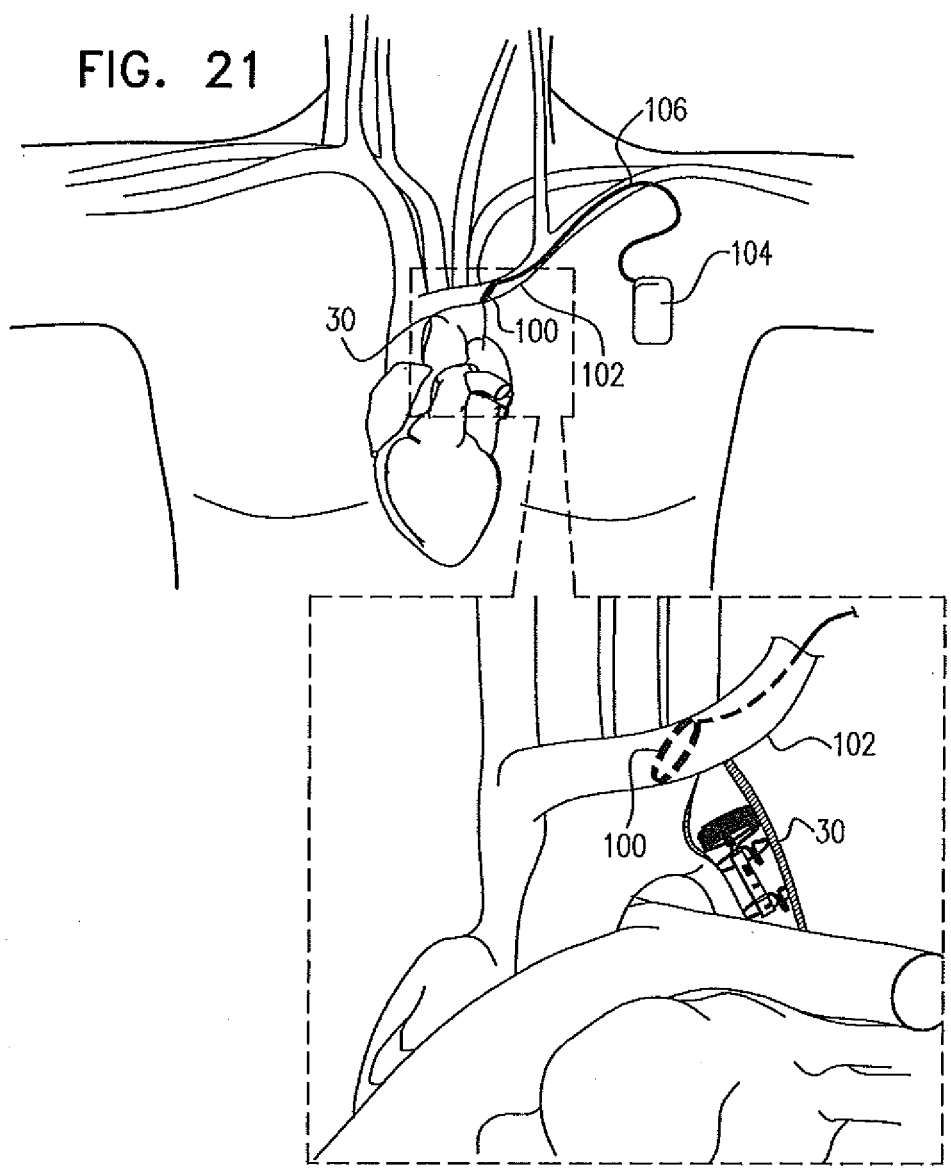
FIG. 21 is a schematic illustration of a transmitter that is placed in a vein that is in the vicinity of an artery in which a stimulating and/or a sensing electrode is placed, in accordance with some applications of the present invention.

Reference is now made to FIG. 21, which is a schematic illustration of a transmitter 100 that is placed in a vein 102 that is in the vicinity of an artery (e.g., aorta 30) in which a stimulating electrode (e.g., electrode 21 and/or electrode 72, described hereinabove) and/or a sensing electrode (e.g., electrode 62, described hereinabove) is placed, in accordance with some applications of the present invention. Alternatively or additionally, transmitter 100 is placed in a vein in the vicinity of the vagus nerve, and the transmitter is used with vagal electrode 20 described hereinabove, *mutatis mutandis*.

For some applications, control unit 66 described hereinabove, and/or a control unit for driving electrode 21 is disposed in a subcutaneously implanted housing 104 (e.g., a titanium housing). For some applications, housing 104 is implanted in the vicinity of the electrode, e.g., within 10 cm of the electrode. For some applications, housing 104 is disposed on a chest belt that is worn on the subject's chest, such that the housing is outside the subject's body, but within 15 cm of the electrode. The control unit wirelessly drives the electrode, receives a signal from the electrode, and/or powers circuitry associated with the electrode (e.g., circuitry 112 described hereinbelow), by transmitting a wireless signal to a receiving coil 114 (FIG. 22) that is coupled to the electrode.

For some applications, the control unit is disposed inside housing 104 and is implanted subcutaneously inside the subject, as described hereinabove. Parameters of the control unit may be adjusted by transmitting a signal to the control unit from outside the subject's body. Alternatively or additionally, electrical power may be supplied to the subcutaneously implanted control unit, by transmitting a signal to the control unit from outside the subject's body.

For some applications, control unit 66 described hereinabove, and/or a control unit for driving electrode 21 is disposed in a subcutaneously implanted housing 104, as described hereinabove. The control unit is coupled, via a lead 106 to transmitter 100 (e.g., a transmitting coil, as shown) that is implanted in a vein (e.g., the subclavian vein) that is in the vicinity of an artery (e.g., aorta 30) in which a stimulating electrode (e.g., electrode 21 and/or electrode 72), described hereinabove) and/or a sensing electrode (e.g., electrode 62, described hereinabove) is placed. The control unit wirelessly drives the electrode, receives a signal from the electrode, and/or powers circuitry 112 associated with the electrode by transmitting a wireless signal to coil 114, which is coupled to the electrode (or receiving a wireless signal from coil 114) via transmitter 100. Typically, the transmitter is placed inside the vein such that it is at a distance from the intra-arterial electrodes of more than 2 mm and/or less than 5 mm (e.g., 2-5 mm), or more than 5 mm and/or less than 20 mm (e.g., 5-20 mm). For example, the transmitter may be placed in the pulmonary vein, innominate vein, vena cava, jugular vein, and/or subclavian vein.

It is noted that for some applications, circuitry 112 (FIG. 22) that is placed intra-arterially drives the intra-arterial electrodes, and/or receives data from the electrodes, and intravenous transmitter 100 is used to power the circuitry, but not to drive or to receive data from the intra-arterial electrodes.

Typically, placement of the transmitter in the vein facilitates transmission of the signal from the control unit to the electrodes, due to the proximity of the vein to the artery in which the electrodes are placed. Further typically, it is preferable for a surgeon to puncture a vein (such as the subclavian vein), in order to place lead 106 into the vein, rather than puncturing an artery (such as the aorta) in order to insert the lead into the artery. For some applications, by placing the transmitter in the vein, electrodes placed inside an artery may communicate with the control unit, and/or receive power from the control unit without requiring puncturing of the artery. Alternatively or additionally, transmitter 100 is placed in the vein for a different reason.

For some applications, transmitter 100 is mounted on a support structure (such as a nitinol ring) in order to orient the transmitter in a suitable orientation for transmitting a signal to coil 114 (FIG. 22), which is coupled to the electrode. For example, the transmitter may include a coil that is mounted to the support structure such that a plane that is defined by the coil is at an angle of greater than 10 degrees from a plane that is perpendicular to the local longitudinal axis of the vein in which the transmitter is placed. Alternatively, the transmitter coil is oriented with respect to the support structure such that the plane defined by the coil is generally perpendicular to the local longitudinal axis of the vein.

For some applications, transmitter coil 100 is placed inside the vein such that the plane defined by the coil is at an angle of greater than 10 degrees from a plane that is perpendicular to the local longitudinal axis of the vein, without mounting the coil on a support structure. Alternatively, the coil is placed inside the vein such that the plane defined by the coil is generally perpendicular to the local longitudinal axis of the vein, without mounting the coil on a support structure. Typically, the transmitter coil is placed in the vein (by being mounted on a support structure, or not by being mounted on a support structure) such that the plane defined by the transmitter coil is generally perpendicular to the plane defined by coil 114, which is placed in the subject's artery.

Figure 22:
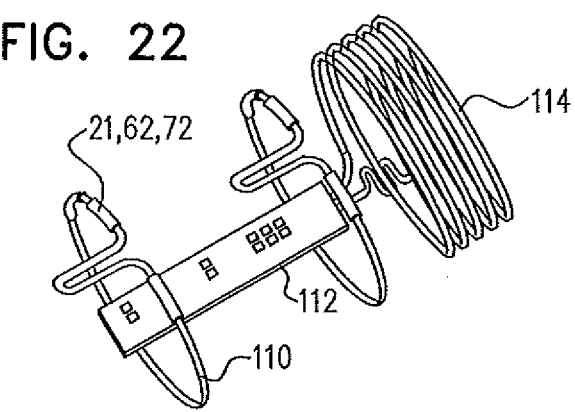
FIG. 22 is a schematic illustration of an electrode configuration for use with the transmitter shown in FIG. 21, in accordance with some applications of the present invention.

Reference is now made to FIG. 22, which is a schematic illustration of an electrode configuration for use with transmitter 100, in accordance with some applications of the present invention. In accordance with respective applications, the electrodes that are used with transmitter 100 may include a stimulating electrode (e.g., electrode 21 and/or electrode 72, described hereinabove) and/or a sensing electrode (e.g., electrode 62, described hereinabove).

The electrodes are configured to be placed in an artery (e.g., aorta 30) by being mounted on support structures, such as nitinol rings 110, as shown. For some applications (not shown), the electrodes are mounted on stent, such as a coil stent, or a mesh stent. A circuit board that includes circuitry 112 for driving the electrodes, and/or for receiving data that are sensed by the electrodes is also mounted on the support structures. A coil 114 is coupled to the circuit board. In accordance with respective applications, coil 114 (a) receives a signal from transmitter 100 and/or directly from a control unit inside housing 104 for driving the electrodes, (b) receives electrical power from transmitter 100 and/or directly from a control unit inside housing 104, and/or (c) transmits data that have been sensed by the electrodes to transmitter 100 and/or directly to a control unit inside housing 104.

Typically, rings 110 (and/or other support structures that are used to support the intra-arterial electrodes) and coil 114 are collapsible, such that the rings and the coil can be implanted transcatheterally in a collapsed configuration. For example, the support structures and the coil may include a shape memory alloy, such as nitinol.

For some applications, the techniques described herein are practiced in combination with techniques described in PCT Publication WO 07/013,065 to Gross, which is incorporated herein by reference. For some applications, the techniques described herein are practiced in combination with the techniques described in PCT application WO 09/095,918, entitled "Peristaltic pump for treatment of erectile dysfunction," to Gross, which claims priority from US Patent Application 2009/0198097 to Gross, the PCT application and the US application being incorporated herein by reference. For some applications, the techniques described herein are practiced in combination with the techniques described in US Patent Application 2009/0198097 to Gross, which is incorporated herein by reference.

For some applications, the methods described herein are performed in combination with the techniques described in PCT Application WO 09/095,920 to Gross, which is incorporated herein by reference.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
an electrode configured to be placed in contact with an aortic site of a subject that is downstream of a bifurcation of the aorta with a left subclavian artery, and between first and fifth intercostal arteries of the subject;
a control unit configured to drive the electrode to perform a function with respect to the site, the function selected from the group consisting of: driving a current into the site, and sensing an electrical parameter of the site; and
a transmitter configured to be placed in a vein of the subject that is in a vicinity of the site, the transmitter being wiredly connected to the control unit, and the control unit being configured to drive the electrode by wirelessly transmitting a signal via the transmitter.

2. The apparatus according to claim 1, wherein the control unit is configured to be subcutaneously implanted inside the subject.

3. The apparatus according to claim 1, wherein the transmitter comprises a coil that defines a plane, and wherein the coil is configured to be placed inside the subject's vein such that the plane defined by the coil is at an angle of more than 10 degrees from a plane that is perpendicular to a local longitudinal axis of the vein.

4. The apparatus according to claim 3, further comprising a coil support structure, the coil being coupled to the support structure such that the support structure is configured to place the coil inside the subject's vein such that the plane defined by the coil is at the angle of more than 10 degrees from the plane that is perpendicular to the local longitudinal axis of the vein.

5. The apparatus according to claim 1, wherein the transmitter is configured to be placed in a subclavian vein of the subject.

6. The apparatus according to claim 1, wherein the transmitter is configured to be placed in the vein such that the transmitter is at a distance of less than 20 mm from the electrode.

7. The apparatus according to claim 6, wherein the transmitter is configured to be placed in the vein such that the transmitter is at a distance of less than 5 mm from the electrode.

8. A method, comprising:
placing an electrode in contact with an aortic site of a subject that is downstream of a bifurcation of the aorta with a left subclavian artery, and between first and fifth intercostal arteries of the subject;
placing in a vein of the subject that is in a vicinity of the site, a transmitter that is wiredly connected to a control unit; and
using the control unit, driving the electrode to perform a function with respect to the site, the function selected from the group consisting of: driving a current into the site, and sensing an electrical parameter of the site, the driving being performed by the control unit wirelessly transmitting a signal via the transmitter.

9. The method according to claim 8, wherein the transmitter includes a coil that defines a plane, and wherein placing the transmitter inside the subject's vein comprises placing the coil inside the subject's vein such that the plane defined by the coil is at an angle of more than 10 degrees from a plane that is perpendicular to a local longitudinal axis of the vein.

10. The method according to claim 8, wherein placing the transmitter inside the vein comprises placing the transmitter inside the vein such that the transmitter is at a distance of less than 20 mm from the electrode.

11. The method according to claim 10, wherein placing the transmitter inside the vein comprises placing the transmitter inside the vein such that the transmitter is at a distance of less than 5 mm from the electrode.

12. The method according to claim 8, wherein placing the transmitter inside the vein comprises placing the transmitter inside a subclavian vein of the subject.

13. The method according to claim 8, wherein placing the electrode in contact with the aortic site comprises placing the electrode in contact with a portion of the aorta that is adjacent to a portion of a vagus nerve of the subject that is between (a) a vagal bifurcation with a thoracic cardiac branch of the subject, and (b) thoracic vagal branching into the esophageal plexus of the subject.

14. The method according to claim 8, wherein driving the electrode to perform the function with respect to the site comprises reducing ventricular pressure of the subject by driving a current into the aortic site via the electrode.

15. The method according to claim 8, wherein driving the electrode to perform the function with respect to the site comprises reducing aortic pressure of the subject by driving a current into the aortic site via the electrode.

16. The method according to claim 8, wherein driving the electrode to perform the function with respect to the site comprises reducing sympathetic tone of the subject by driving a current into the aortic site via the electrode.

17. The method according to claim 8, wherein driving the electrode to perform the function with respect to the site comprises increasing parasympathetic tone of the subject by driving a current into the aortic site via the electrode.

18. The method according to claim 8, wherein driving the electrode to perform the function with respect to the site comprises reducing sympathetic tone and increasing parasympathetic tone of the subject by driving a current into the aortic site via the electrode.

19. The method according to claim 8, wherein driving the electrode to perform the function with respect to the site comprises increasing aortic compliance of the subject by driving a current into the aortic site via the electrode.

20. The method according to claim 8, wherein placing the electrode in contact with the aortic site comprises assessing a response of the subject to placement of the electrode at a plurality of sites, and implanting the electrode at the aortic site in response to the assessing.

21. The method according to claim 8, wherein driving the electrode to perform the function with respect to the site comprises reducing a ratio of a low frequency component to a high frequency component of heart rate variability of the subject by driving a current into the aortic site via the electrode.

22. The method according to claim 21, wherein the low frequency component is less than 0.05 Hz, and wherein the high frequency component is between 0.15 and 0.35 Hz.

23. The method according to claim 8, wherein driving the electrode to perform the function with respect to the site comprises reducing a ratio of a low frequency component to a high frequency component of blood pressure variability of the subject by driving a current into the aortic site via the electrode.

24. The method according to claim 23, wherein the low frequency component is less than 0.05 Hz, and wherein the high frequency component is between 0.15 and 0.35 Hz.

25. The apparatus according to claim 1, wherein the transmitter is configured to be placed in a vena cava of the subject.

26. The method according to claim 8, wherein placing the transmitter inside the vein comprises placing the transmitter inside a vena cava of the subject.

* * * * *